(12) United States Patent
Carmel et al.

(10) Patent No.: US 9,168,084 B2
(45) Date of Patent: Oct. 27, 2015

(54) BRAZED ELECTROSURGICAL DEVICE

(75) Inventors: Yuval Carmel, Rockville, MD (US); Anatoly Shkvarunets, Rockville, MD (US); Robert A. Van Wyk, St. Pete Beach, FL (US)

(73) Assignee: ElectroMedical Associates, LLC, Bethesda, MD (US)

( * ) Notice: Subject to any disclaimer, the term of this patent is extended or adjusted under 35 U.S.C. 154(b) by 1087 days.

(21) Appl. No.: 13/104,424

(22) Filed: May 10, 2011

(65) Prior Publication Data
US 2011/0282341 A1 Nov. 17, 2011

Related U.S. Application Data

(60) Provisional application No. 61/395,276, filed on May 11, 2010.

(51) Int. Cl.
*A61B 18/14* (2006.01)
*A61B 17/00* (2006.01)
(Continued)

(52) U.S. Cl.
CPC ............ *A61B 18/14* (2013.01); *A61B 18/149* (2013.01); *A61B 19/5225* (2013.01); *A61B 2017/0088* (2013.01); *A61B 2017/00526* (2013.01); *A61B 2018/00083* (2013.01);
(Continued)

(58) Field of Classification Search
CPC .......... A61B 18/14; A61B 2018/1475; A61B 2018/1405; A61B 2018/00107; A61B 2018/1467; A61B 1018/1415; A61B 1018/1432; A61B 18/149; A61B 19/5225; A61B 2017/00526; A61B 2017/0088; A61B 2017/00083; A61B 2018/1472; A61B 2018/1495; A61B 2218/002

USPC ........................................................ 606/41
See application file for complete search history.

(56) References Cited

U.S. PATENT DOCUMENTS 2,448,741 A    9/1948  Scott et al.
3,838,242 A *  9/1974  Goucher ................. 219/121.36
(Continued)

OTHER PUBLICATIONS www.WiseTool.com, Coefficient of Thermal Expansion, 2014 (date accessed).*

*Primary Examiner* — Linda Dvorak
*Assistant Examiner* — Yasamin Ekrami
(74) *Attorney, Agent, or Firm* — Smith Patent; Chalin A. Smith

(57) ABSTRACT

Disclosed herein is a distal end electrode assembly for use in connection with electrosurgical devices, particularly those adapted for the modification, sculpting, resection, removal, or vaporization of tissue, configured for coagulation, cauterization or hemostasis purposes, or utilized for thermal treatment of normal and tumorous tissues. In the context of the present invention, mechanical fastening means, epoxies and other high-temperature adhesives connecting electrode(s) to insulator(s) are replaced with brazed joints to yield electrosurgical devices capable of safely and reliably operating at high power densities and elevated temperatures without thermal failure of the bonds between the electrode and the insulator. The use of brazed joints further permits the construction of miniaturized, compact electrosurgical devices, of both monopolar and bipolar configurations, having utility in a number of divergent fields, from arthroscopy to otolaryngology to oncology, and applicable to both laparoscopic and open surgery techniques. Thus, active electrodes and electrosurgical devices of the present invention maximize efficiency, safety and reliability while minimizing manufacturing cost and device profile.

35 Claims, 19 Drawing Sheets

(51) Int. Cl.
  *A61B 19/00* (2006.01)
  *A61B 18/00* (2006.01)

(52) U.S. Cl.
  CPC  *A61B 2018/1472* (2013.01); *A61B 2018/1475* (2013.01); *A61B 2018/1495* (2013.01); *A61B 2218/002* (2013.01)

(56) References Cited

U.S. PATENT DOCUMENTS

| | | | |
|---|---|---|---|
| 3,856,015 A | 12/1974 | Iglesias | |
| 3,901,242 A | 8/1975 | Storz | |
| 4,674,499 A | 6/1987 | Pao | |
| 4,682,596 A | 7/1987 | Bales | |
| 4,726,370 A | 2/1988 | Karasawa | |
| 4,832,048 A | 5/1989 | Cohen | |
| 4,917,082 A | 4/1990 | Grossi et al. | |
| 5,195,959 A | 3/1993 | Smith | |
| 5,261,905 A | 11/1993 | Doresey, III | |
| 5,277,696 A | 1/1994 | Hagen | |
| 5,300,068 A * | 4/1994 | Rosar et al. | 606/34 |
| 5,314,459 A | 5/1994 | Swanson et al. | |
| 5,320,635 A * | 6/1994 | Smith | 606/180 |
| 5,342,381 A * | 8/1994 | Tidemand | 606/174 |
| 5,573,532 A * | 11/1996 | Chang et al. | 606/26 |
| 5,582,610 A | 12/1996 | Grossi et al. | |
| 5,598,966 A * | 2/1997 | Romano et al. | 228/124.6 |
| 5,647,840 A | 7/1997 | D'Amelio et al. | |
| 5,681,282 A | 10/1997 | Eggers et al. | |
| 5,688,269 A * | 11/1997 | Newton et al. | 606/46 |
| 5,697,536 A | 12/1997 | Eggers et al. | |
| 5,709,698 A | 1/1998 | Adams et al. | |
| 5,782,829 A | 7/1998 | Swiantek et al. | |
| 5,782,891 A * | 7/1998 | Hassler et al. | 607/36 |
| 6,033,400 A | 3/2000 | Grossi et al. | |
| 6,053,923 A * | 4/2000 | Veca et al. | 606/80 |
| 6,066,134 A | 5/2000 | Eggers | |
| 6,113,597 A | 9/2000 | Eggers et al. | |
| 6,169,926 B1 | 1/2001 | Baker | |
| 6,181,760 B1 * | 1/2001 | JinKim | 376/245 |
| 6,197,025 B1 | 3/2001 | Grossi et al. | |
| 6,222,307 B1 * | 4/2001 | Roy et al. | 313/326 |
| 6,235,020 B1 | 5/2001 | Cheng et al. | |
| 6,277,114 B1 | 8/2001 | Bullivant et al. | |
| 6,296,638 B1 | 10/2001 | Davison et al. | |
| 6,379,350 B1 | 4/2002 | Sharkey et al. | |
| 6,379,351 B1 | 4/2002 | Thapliyal et al. | |
| 6,391,025 B1 | 5/2002 | Weinstein et al. | |
| 6,419,684 B1 | 7/2002 | Heisler et al. | |
| 6,468,274 B1 | 10/2002 | Alleyne et al. | |
| 6,514,248 B1 | 2/2003 | Eggers et al. | |
| 6,565,560 B1 | 5/2003 | Goble et al. | |
| 6,575,968 B1 * | 6/2003 | Eggers et al. | 606/41 |
| 6,582,423 B1 | 6/2003 | Thapliyal et al. | |
| 6,589,237 B2 | 7/2003 | Woloszko | |
| 6,767,347 B2 | 7/2004 | Sharkey et al. | |
| 6,770,070 B1 | 8/2004 | Balbierz | |
| 6,796,982 B2 | 9/2004 | Carmel et al. | |
| 6,837,884 B2 | 1/2005 | Woloszko | |
| 6,840,937 B2 | 1/2005 | Van Wyk | |
| 6,899,712 B2 | 5/2005 | Moutafis et al. | |
| 6,920,883 B2 | 7/2005 | Bessette et al. | |
| 6,921,398 B2 | 7/2005 | Carmel et al. | |
| 6,921,399 B2 | 7/2005 | Carmel et al. | |
| 6,955,676 B2 | 10/2005 | Quick | |
| 7,066,936 B2 | 6/2006 | Ryan | |
| 7,118,574 B2 * | 10/2006 | Patel et al. | 606/80 |
| 7,150,748 B2 | 12/2006 | Ebbutt et al. | |
| 7,160,296 B2 * | 1/2007 | Pearson et al. | 606/42 |
| 7,166,103 B2 | 1/2007 | Carmel et al. | |
| 7,244,263 B2 * | 7/2007 | Robison et al. | 606/170 |
| 7,435,247 B2 * | 10/2008 | Woloszko et al. | 606/41 |
| 7,566,333 B2 | 7/2009 | Van Wyk et al. | |
| 7,611,509 B2 | 11/2009 | Van Wyk | |
| 7,618,428 B2 * | 11/2009 | O'Quinn et al. | 606/159 |
| 7,794,456 B2 * | 9/2010 | Sharps et al. | 606/32 |
| 7,837,683 B2 | 11/2010 | Carmel et al. | |
| 8,055,336 B1 * | 11/2011 | Schulman et al. | 607/2 |
| 8,192,432 B2 * | 6/2012 | McGaffigan | 606/49 |
| 2001/0001314 A1 | 5/2001 | Davison et al. | |
| 2002/0038122 A1 | 3/2002 | Peters et al. | |
| 2002/0052600 A1 * | 5/2002 | Davison et al. | 606/41 |
| 2002/0072745 A1 | 6/2002 | Truckai et al. | |
| 2002/0120261 A1 | 8/2002 | Morris et al. | |
| 2002/0133148 A1 | 9/2002 | Daniel et al. | |
| 2002/0133149 A1 | 9/2002 | Bessette | |
| 2002/0146090 A1 * | 10/2002 | Chornenky et al. | 378/65 |
| 2003/0083655 A1 | 5/2003 | Van Wyk | |
| 2003/0088243 A1 * | 5/2003 | Carmel et al. | 606/41 |
| 2003/0120269 A1 | 6/2003 | Bessette et al. | |
| 2003/0146206 A1 * | 8/2003 | Tanaka et al. | 219/541 |
| 2003/0211407 A1 * | 11/2003 | Watanabe et al. | 430/17 |
| 2004/0006336 A1 | 1/2004 | Swanson | |
| 2004/0006339 A1 | 1/2004 | Underwood et al. | |
| 2004/0027034 A1 * | 2/2004 | Kawaguchi et al. | 310/334 |
| 2004/0030330 A1 | 2/2004 | Brassel et al. | |
| 2004/0046557 A1 * | 3/2004 | Karmarkar et al. | 324/322 |
| 2004/0049183 A1 | 3/2004 | Ellman et al. | |
| 2004/0088032 A1 * | 5/2004 | Haller et al. | 607/116 |
| 2004/0104455 A1 | 6/2004 | Shimizu | |
| 2004/0106919 A1 | 6/2004 | Hood | |
| 2004/0136499 A1 * | 7/2004 | Holland et al. | 378/119 |
| 2004/0181251 A1 * | 9/2004 | Hacker et al. | 606/170 |
| 2004/0193150 A1 | 9/2004 | Sharkey et al. | |
| 2004/0230190 A1 | 11/2004 | Dahla et al. | |
| 2005/0065510 A1 | 3/2005 | Carmel et al. | |
| 2005/0228467 A1 * | 10/2005 | Jiang | 607/115 |
| 2005/0234165 A1 | 10/2005 | Van Wyk et al. | |
| 2005/0240229 A1 * | 10/2005 | Whitehurst et al. | 607/2 |
| 2005/0277915 A1 | 12/2005 | DeCesare et al. | |
| 2006/0122680 A1 | 6/2006 | Auth et al. | |
| 2006/0153337 A1 * | 7/2006 | Holland et al. | 378/144 |
| 2006/0184165 A1 | 8/2006 | Webster et al. | |
| 2006/0212030 A1 | 9/2006 | McGaffigan | 606/27 |
| 2006/0217703 A1 * | 9/2006 | Chornenky et al. | 606/41 |
| 2006/0224154 A1 | 10/2006 | Shadduck et al. | |
| 2006/0235377 A1 | 10/2006 | Earley et al. | |
| 2006/0259031 A1 | 11/2006 | Carmel et al. | |
| 2006/0271109 A1 * | 11/2006 | Kuzma et al. | 607/2 |
| 2006/0293653 A1 | 12/2006 | Van Wyk | |
| 2008/0077129 A1 | 3/2008 | Van Wyk et al. | |
| 2008/0121419 A1 * | 5/2008 | Haller et al. | 174/260 |
| 2008/0131723 A1 * | 6/2008 | Tucker et al. | 428/623 |
| 2008/0208189 A1 | 8/2008 | Van Wyk et al. | |
| 2008/0269596 A1 * | 10/2008 | Revie et al. | 600/424 |
| 2009/0069802 A1 | 3/2009 | Garito et al. | |
| 2010/0015491 A1 * | 1/2010 | Yamanis | 429/30 |
| 2010/0023000 A1 * | 1/2010 | Stevenson et al. | 606/33 |
| 2010/0140330 A1 * | 6/2010 | Chatterjee et al. | 228/122.1 |
| 2010/0152724 A1 * | 6/2010 | Marion et al. | 606/33 |
| 2010/0160910 A1 * | 6/2010 | Kramer et al. | 606/41 |

\* cited by examiner

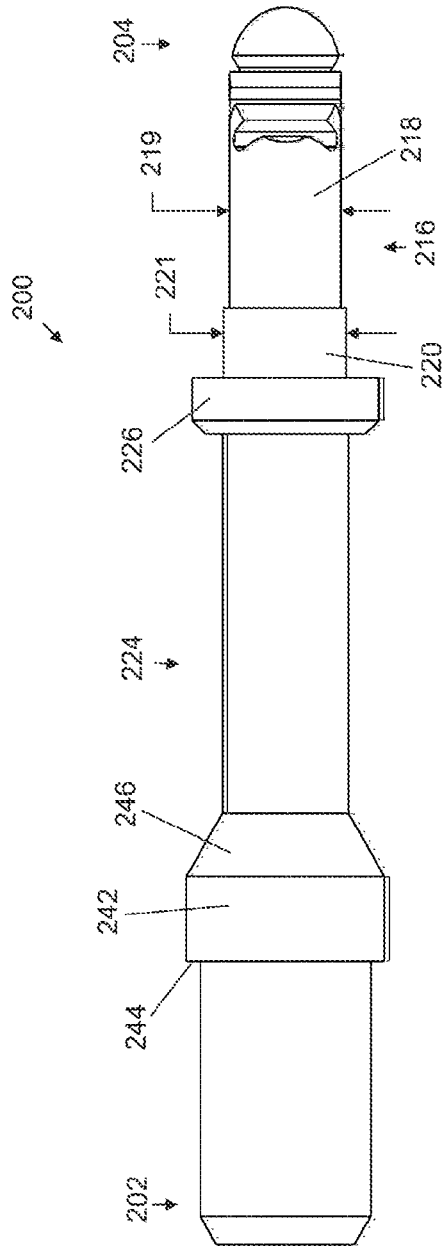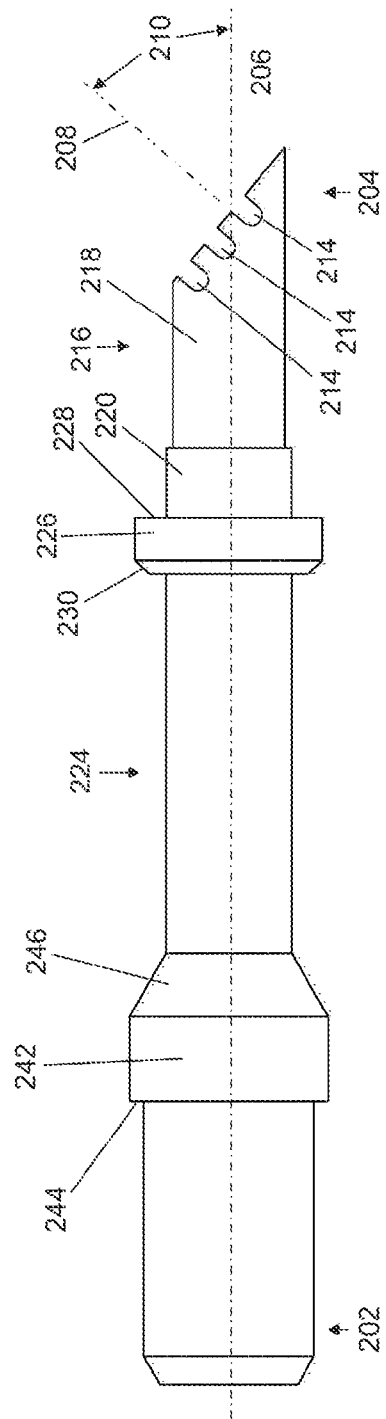
Fig. 5
Fig. 6

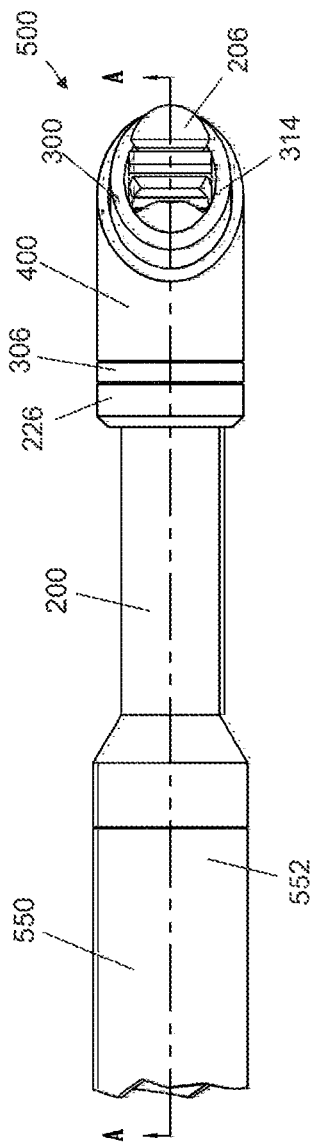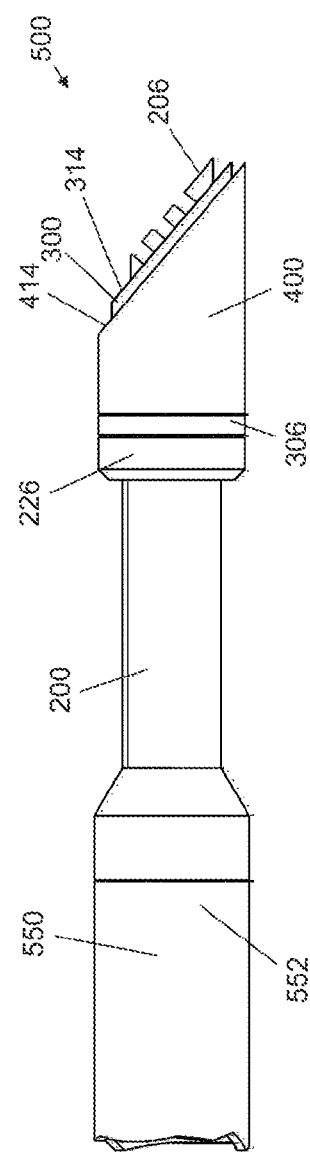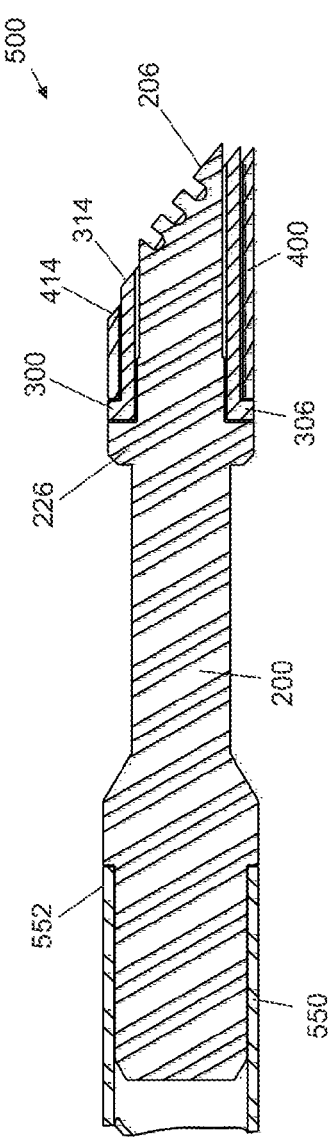

A-A

BRAZED ELECTROSURGICAL DEVICE

PRIORITY

This application claims the benefit of U.S. Provisional Application Ser. No. 61/395,276, filed May 11, 2010, the entire contents of which are hereby incorporated by reference herein.

FIELD OF THE INVENTION

The present invention relates to the field of electrosurgery, and more specifically to electrosurgical devices adapted for the modification, sculpting, resection, removal, or vaporization of tissue, configured for coagulation, cauterization or hemostasis purposes, or utilized for thermal treatment of normal and tumorous tissues that employ ceramic to metal brazing in the assembly process. The devices fabricated in accordance with the principles of this invention are suitable for a number of medical applications, both in conductive and non-conductive fluids as well as in dry and semi-dry environments, with or without aspiration.

BACKGROUND OF THE INVENTION

Minimally invasive surgical techniques have gained significant popularity due to their ability to accomplish desirable outcomes with reduced patient pain and accelerated recovery and return of the patient to normal activities. Arthroscopic surgery, wherein the intra-articular space is filled with fluid, allows orthopedic surgeons to efficiently perform procedures using special purpose instruments designed specifically for arthroscopy. Among these special purpose tools are various manual graspers and biters, powered shaver blades and burs, and electrosurgical devices. During the last several years, specialized arthroscopic electrosurgical electrodes referred to in the art as "ablators" have been developed. Examples of such instruments include "ArthroWands" manufactured by Arthrocare (Austin, Tex.), VAPR electrodes manufactured by Depuy Mitek (Raynham, Mass.) and electrodes by Smith and Nephew, Inc. (Andover, Mass.). These ablator electrodes differ from conventional arthroscopic electrosurgical electrodes in that they are designed for the bulk removal of tissue by vaporization rather than the cutting of tissue or coagulation of bleeding vessels. While standard electrodes are capable of ablation, their geometries are generally not efficient for accomplishing this task. The tissue removal rates of ablator electrodes are lower than those of arthroscopic shaver blades, however, electrosurgical ablators are used because they achieve hemostasis (stop bleeding) during use and are able to efficiently remove tissue from bony surfaces. Ablator electrodes are used in an environment filled with electrically conductive fluid.

During ablation, current flows from the ablator into the conductive fluid and locally heats the fluid to its boiling point. The relative heating of the conductive fluid is proportional to the density of electrical current flowing from the electrode into the fluid. Regions of high current density will experience higher rates of heating as compared to regions of low current density. In general, regions of high current density occur at the corners and edges of the electrode. Steam bubbles form first at the edges of an ablator but eventually cover virtually the electrode's entire exposed surface. When a steam bubble reaches a critical size, arcing occurs within the bubble and enclosed portion of tissue. A train of sparks occurs within the bubble with the train ending when the bubble grows too large or the tissue enclosed in the bubble is evaporated and conditions within the bubble become unfavorable for sparking.

During ablation, water within the target tissue is vaporized. Because volumes of tissue are vaporized rather than discretely cut out and removed from the surgical site, the power requirements of ablator electrodes are generally higher than those of other arthroscopic electrosurgical electrodes. The efficiency of the electrode design and the characteristics of the Radio Frequency (RF) power supplied to the electrode also affect the amount of power required for ablation. Electrodes with inefficient designs and/or powered by RF energy sources with poorly suited characteristics will require higher power levels than those with efficient designs and appropriate generators. Because of these factors, the ablation power levels of devices produced by different manufacturers vary widely with some using power levels significantly higher than those commonly used by arthroscopists. Ablator electrode systems from some manufacturers may use up to 400 Watts, significantly higher than the 30 to 70 Watt range generally used by other arthroscopic electrosurgical electrodes.

During arthroscopic electrosurgery, all of the RF energy supplied to the electrode is converted into heat, thereby raising the temperature of the fluid within the joint and the temperature of adjacent tissue. Prior to the introduction of ablator electrodes, the temperature of the fluid within the joint was not of concern to the surgeon. However, due to the higher power levels at which they generally operate and the longer periods of time that they are energized, fluid temperature is a major concern during the use of ablator electrodes. Standard arthroscopic electrosurgical electrodes are usually energized for only brief periods, generally measured in seconds, while specific tissue is resected or modified, or a bleeder coagulated. In contrast, ablator electrodes are energized for longer periods of time, often measured in minutes, while volumes of tissue are vaporized.

The temperature of the fluid within the joint is critical since nerve damage and cell death can occurs at tissue temperatures as low as 45-50° C., a temperature easily reached with high-powered ablators if fluid flow through the surgical site is insufficient. Patient injury may result. Such injuries have been documented.

The likelihood of thermal injury is strongly affected by the amount of power supplied to the ablator. This, in turn, is determined by the efficiency of the ablator and the speed with which the surgeon desires to remove tissue. A highly efficient ablator will allow the surgeon to remove tissue at desirably high rates while requiring low levels of power input. Under these conditions, the likelihood of thermal injuries is reduced significantly.

Ablator electrodes are produced in a variety of sizes and configurations to suit a variety of procedures. For example, ablators designed for use in ankle, wrist or elbow arthroscopy are generally smaller than those used in the knee or shoulder. Each size embodiment is then produced in a variety of configurations to facilitate access to various structures within the joint being treated. These configurations differ in terms of the working length of the electrode (i.e., the maximum distance that an electrode can be inserted into a joint), the size and shape of the ablating surfaces and the angle between the ablating face and the axis of the electrode shaft. Electrodes are typically designated by the angle between a normal to the ablating surface and the axis of the electrode shaft, and by the size of their ablating surface and any associated insulator.

Primary considerations of surgeons when choosing a particular configuration of ablator for a specific procedure include its convenience of use (i.e., the ease with which the instrument is able to access certain structures) and the speed with which the ablator will be able to complete the required tasks. When choosing between two configurations capable of accomplishing a particular task, surgeons will generally choose the ablator with the larger ablating surface so as to remove tissue more quickly. This is particularly true for procedures during which large volumes of tissue must be removed. One such procedure is acromioplasty, the reshaping of the acromion. The underside of the acromion is covered with highly vascular tissue that may bleed profusely when removed by a conventional powered cutting instrument, such as an arthroscopic shaver blade. Ablator electrodes are used extensively during this procedure since they are able to remove tissue without the bleeding which obscures the surgeon's view of the site. Ablation in the area under the acromion is most efficiently accomplished using an electrode on which a line normal to the ablating surface is approximately perpendicular to the axis of the ablator shaft. Such an electrode is referred to in the field as a "90 Degree Ablator" or a "side effect" ablator. Examples of such electrodes include the "3.2 mm 90 Degree Three-Rib UltrAblator" by Linvatec Corporation (Largo, Fla.), the "90 Degree Ablator" and "90 Degree High Profile Ablator" by Smith and Nephew (Andover, Mass.), the "Side Effect VAPR Electrode" by Depuy Mitek (Raynham, Mass.), and the "3.5 mm 90 Degree Arthrowand", "3.6 mm 90 Degree Lo Pro Arthrowand", and "4.5 mm 90 Deg. Eliminator Arthrowand" by Arthrocare Corporation, and "3 mm OPES Ablator" and "4 mm OPES Ablator" and others by Arthrex (Naples, Fla.).

Recently ablator electrodes have been configured with mechanism and means for removing bubbles and debris from the surgical site. During electrosurgery in a conductive fluid environment, tissue is vaporized producing steam bubbles that may obscure the view of the surgeon or displace saline from the area of the intra-articular space that the surgeon wishes to affect. In the case of ablation (i.e., bulk vaporization of tissue), the number and volume of bubbles produced is even greater than when using other electrodes since fluid is continually boiling at the active electrode during use. Ideally, flow through the joint carries these bubbles away; however, in certain procedures, this flow is insufficient to remove all of the bubbles. Accordingly, the ablator is configured with an aspiration means that removes some bubbles as they are formed by the ablation process, and others after they have collected in pockets within the joint. The ablator aspiration means is typically connected to an external vacuum source that provides suction for bubble evacuation. An illustrative example of an aspirating ablator is described by Carmel, et al. in U.S. Pat. No. 7,837,683 issued Nov. 23, 2010, the contents of which are incorporated by reference herein. While Carmel suggests positioning an aspiration port in the center of the active electrode, other aspirating schemes are contemplated. See, for example, the flexible aspirating ablators described in a co-pending application to Van Wyk, U.S. Ser. No. 13/091,584 filed Apr. 21, 2011, the contents of which are incorporated by reference herein.

The construction of ablators may be generally separated into two categories: (a) those with simple construction in which the RF energy is conducted to the active electrode by the distally extending structural member, and (b) those with complex construction in which the RF energy is conducted to the active electrode by wires within a tubular distally extending structural member. Examples of simple construction ablators include the monopolar devices marketed by Linvatec, Arthrex and Smith and Nephew. Examples of complex construction ablators include those marketed by Arthrocare, DePuy Mitek, Stryker Corporation (San Jose, Calif.) and the bipolar ablators marketed by Smith and Nephew. All bipolar devices are necessarily categorized as a "complex construction" necessitated by the presence of both active and return electrodes at the vicinity of the electrode distal tip.

Arthroscopic ablators have a distal end construction in which an active electrode is surrounded by a ceramic insulator that covers the active electrode, with the exception of the exposed ablating surface that generally protrudes beyond the insulator a short distance. The axial positioning of the insulator generally is maintained by a flange on the active electrode, the flange typically having a distally facing surface against which the proximal end of the insulator is positioned. The insulator is generally held in place by an adhesive (typically, an epoxy) and/or by a dielectric coating that covers the elongated distal element of the ablator and overlaps the proximal end of the insulator. The dielectric coating is frequently applied as a powder that is then fused to the device by curing at an elevated temperature.

Heat from the ablating arcs heats the active electrode. Indeed, the arcs vaporize portions of the active electrode on which the arcing occurs such that the ablating surface and its features are eroded during use. Heat from the arcs flows into the active electrode raising the temperature of the active electrode and the adjacent insulator. In the case of ablators of simple construction, wherein the insulator is retained on the assembly by an adhesive or polymeric coating, the local elevation of electrode and insulator temperatures may result in the melting or degradation of the adhesive or coating. This is particularly true in the region in which the proximal face of the insulator contacts the flange of the active electrode, as the protruding discontinuity of the active electrode surface at this location tends to result in a concentration of the electric field. High temperatures at this location, combined with the intensified electric field, may cause a premature breakdown of the insulating polymeric coating so that arcing occurs between the underlying electrode at this location and the conductive fluid surrounding the ablator. After initial breakdown of the insulating coating, arcing at the location destroys adjacent coating and the opening in the coating grows. Arcing at this location causes additional heating of the active electrode and insulator frequently leading to catastrophic failure of the coating. This catastrophic failure frequently destroys the bond between the active electrode and the insulator, thereby allowing the insulator to fall off of the assembly into the patient's joint. The high temperature resulting from coating failure may also cause thermal gradients within the insulator that may, in turn, cause it to break apart. As accident reports documented by the database maintained by the Food and Drug Administration (FDA) demonstrate, insulator pieces frequently fall into the patient's joint. When the insulator or parts thereof fall into a patient's joint space, the surgeon must retrieve the foreign bodies from the site. This can be easily accomplished if the foreign bodies are ejected into a site where they are visible. However, in many cases, the pieces fall into locations that are hidden from view and the surgeon must do an extensive search, a process that frequently involves bringing an imaging system into the operating room or, in some cases, converting the minimally invasive procedure to a full open surgical procedure. The task of retrieving pieces that fall into the patient body is further complicated by the fact that such pieces cannot be easily detected by various X-ray or fluoroscopy imaging systems. This can cause lengthy delays in the surgery, and in some cases, can result in the insulator or insulator fragments remaining in the body of the patient after the surgery. Obviously, neither of these unintended consequences is desirable.

To prevent failure of the polymeric coating and adhesive, and therefore to increase patient safety by increasing the reliability of electrosurgical devices, it is desirable to use coatings and adhesives with high service temperatures. However, the selected material must also be biocompatible. The dielectric coating that covers the elongate distal member and overlaps the proximal end of the insulator may be applied electrostatically as a powder and cured at elevated temperature or, alternatively, may be a tubular "heat shrink" material, i.e., an extruded polymeric tube that is positioned on the device and then shrunk in place using heat. While a cured powder coating is able to both cover the tube and provide a means for retaining the insulator in position, use of the heat shrink material requires the use of an additional adhesive to retain the insulator in position. If the adhesive fails due to excessive heating during use, the heat shrink tubing provides little retaining force on the insulator, and the insulator is thus easily ejected into the joint. Nevertheless, biocompatible heat-shrink materials are available with high dielectric strengths and service temperatures higher than those of biocompatible powder coatings thereby making the use of heat-shrink materials desirable on electrosurgical devices when possible.

The temperature of the active electrode/insulator assembly may be minimized through efficient dispersal of heat from the active electrode. With non-aspirating electrodes, the heat may be conducted proximally into the elongate member by maximizing the device cross-section proximal to the insulator so as to allow effective heat conduction. In the case of aspirating ablators, the flow through the device may be maximized to provide effective convective cooling of the electrode. The flow is limited, however, by the size of the aspiration port, and cooling of the assembly may be limited by the presence of any dielectric coating on the inside of the aspiration lumen.

A novel means to prevent ejection of an insulator from an electrosurgical ablator into a patient is described in DeCesare et al. in U.S. Pat. No. 7,150,746 issued Dec. 19, 2006. Therein, a flange is provided on the distal portion of the active electrode to prevent the insulator from slipping distally off of the active electrode in the event of coating failure. While this is effective, it requires a unique construction not applicable to all types of ablators, and further requires increasing the size of the device distal end beyond what may be desirable in many applications.

Indeed, it is desirable to make the distal end of an ablator as small as is practically possible so as to minimize the requisite diameter of the introductory canola and thereby minimize trauma to the joint space. Also, ablating tissue in tight spaces like the wrist and elbow requires the use of a small ablator, the smaller sizes affording the surgeon with greater maneuverability in the joint space. Accordingly, the design options for an arthroscopy ablator are limited by thermal concerns and the inability to use mechanical fastening means to affix the insulator to the active electrode except in extremely limited circumstances.

However, the afore-mentioned problems are not unique to arthroscopy ablators. Other medical applications require the construction of electrosurgical devices that are very small in size, yet reliable and safe for the patient. For instance, in the field of urology, in the context of treating benign prostatic hyperplasia (BPH), a condition commonly referred to as "enlarged prostate", the ablators must be sufficiently small to pass through the lumen of a resectoscope inserted into the urethra of a patient. One such device is by Carmel et al. in WO 2008/039746 published Apr. 3, 2008, the contents of which are incorporated by reference herein. These resectoscopes generally have lumens measuring less than 0.3 inches (7.5 mm) and accommodate an optic used to view the surgical site as well as the ablator used to treat tissue. As with arthroscopy ablators, the portion of the active electrode element forming the ablating surface is exposed and the rest of the element is covered by an insulator, preferably fabricated of a non-conductive ceramic material. Because the electrode assembly of an ablator used in a resectoscope is mounted to the distal end of two wires of small cross-section, there is little conductive removal of heat from the assembly, and aspiration flow is not present.

Accordingly, the electrode assembly of an electrosurgical device for tissue vaporization and coagulation used with a resectoscope is frequently heated to temperatures higher than those of arthroscopy ablators, beyond the temperature at which polymeric adhesives provide a reliable bond between the active electrode and insulator. Because the assemblies are very small, it is extremely difficult to mechanically affix the insulator to the active electrode, and doing so unacceptably limits design choices. The problem is compounded if the device is bipolar, with the return electrode also mounted to the insulator, or if the device employs a "floating electrode" as described by Carmel in the above-referenced pending application or in the context of U.S. Pat. Nos. 7,563,261 and 7,566,333, issued Jul. 21, 2009 and Jul. 28, 2009, respectively, the contents of which are incorporated by reference herein.

Accordingly, there is a significant need in the art to improve the affixation of insulator to electrode in the context of electrosurgical devices, particularly those adapted for the modification, sculpting, resection, removal, or vaporization of tissue, configured for coagulation, cauterization or hemostasis purposes, or utilized for thermal treatment of tumors as well as normal tissues. The process should allow the use of heat-shrink materials for insulating of the elongate distal element and proximal portion of the electrode element. At the same time, there is a significant need in the art for the miniaturization of electrosurgical devices without sacrificing the safety and reliability of the device. This is especially important in the context of ablation devices, since the tendency of many electrosurgical vendors is to employ higher and higher electrical power levels, currently as much as 400 Watt, in order to achieve the desired clinical results.

SUMMARY OF THE INVENTION

It is accordingly an object of this invention to provide an electrosurgical device of simple, reliable construction that overcomes the deficiencies discussed above. More particularly, it is an object of the present invention to provide an electrosurgical device capable of operating at high power densities in which the requisite ceramic insulator is affixed to one or more metal electrodes by means of brazing. In that mechanical fastening means are not required, the resulting assembled device may be extremely compact. Moreover, the device may have a much larger margin of safety because it can be reliably operated at much higher temperatures than those in which the insulator and electrode(s) are joined by epoxy or other high-temperature adhesives, or which are held together by a polymeric powder-coat.

It is further an object of this invention to allow for the construction of miniaturized, compact electrosurgical devices, of both monopolar or bipolar configurations, having utility in a number of divergent fields, from arthroscopy to otolaryngology to oncology, and applicable to both laparoscopic and open surgery techniques. The devices based on the principles of this invention may be used in various environments, including electrically conductive and non-conductive liquids and gases as well as dry and semi-dry fields.

It is additionally an object of this invention to provide an electrosurgical ablator of simple compact construction capable of use at high temperatures without thermal failure of the device.

These and other objects are accomplished in the invention herein disclosed, directed to an electrosurgical device of simple construction in which the insulator and at least one electrode are permanently affixed to each other by means of a brazed joint formed there between. It will be understood by those skilled in the art that one or more aspects of this invention can meet certain of the above objectives, while one or more other aspects can meet certain other objectives. Each objective may not apply equally, in all its respects, to every aspect of this invention. As such, the preceding and foregoing objects should be viewed in the alternative with respect to any one aspect of this invention.

In a preferred embodiment, the present invention provides an assembled electrosurgical device in which a first electrode (hereinafter referred to as an "active electrode"), a second electrode (generally a "floating electrode" or "return electrode"), and an interdisposed non-conductive insulator are affixed to each other by brazed joints. In a first preferred embodiment, the active electrode is disposed at the distal end of an elongated conductive member, the proximal end of which is affixed to a handle, the configuration being suitable for, for instance, arthroscopy, laparoscopy, or otolaryngology. The insulator and electrodes are preferably a cylindrical and/or tubular form. With the exception of that portion of the electrode that protrudes beyond the insulator distal surface, the electrode and elongate member are insulated by a dielectric coating that overlaps the proximal end of the insulator. Preferably, the dielectric coating is a high-dielectric polymeric heat-shrink tubing having a high service temperature. The assembled ablator so formed may be used at elevated temperatures without thermal failure of the bonds between the electrodes and the insulator. If the polymeric coating fails (due to electrical and thermal stress) and arcing through the coating occurs, the ablator is no longer useable; however, the insulator/electrode assembly remains intact and thus no loose components or parts thereof may be ejected into the joint-space.

In a second preferred embodiment, the device is configured for use with a resectoscope, as for urology. Due to constraints arising from the use of a resectoscope, the electrodes and insulator have primarily a bi-lateral symmetry and are not formed form cylindrical and/or tubular components. However, as with the previously described preferred embodiment, the electrodes are affixed to the insulator by a bond formed by brazing, the configuration of the braze joint being determined by the materials of the components to be joined.

In the context of either above-described preferred embodiment, the second electrode may be "floating" (i.e., not connected to the electrosurgical generator) or may be connected to the generator so as to function as a "return electrode". In other embodiments, the electrosurgical device may be provided only a first active electrode.

The above-noted objects and features of the invention will become more fully apparent when the following detailed description is read in conjunction with the accompanying figures and/or examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention.

Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of electrode design. Such objects, features, benefits and advantages will be apparent from the above in conjunction with the accompanying examples, data, figures and all reasonable inferences to be drawn there-from, alone or with consideration of the references incorporated herein.

BRIEF DESCRIPTION OF THE FIGURES

Various aspects and applications of the present invention will become apparent to the skilled artisan upon consideration of the brief description of the figures and the detailed description of the present invention and its preferred embodiments that follows:

FIG. 5 is a plan view of a distal end element (active electrode) for an electrosurgical ablator formed in accordance with the principles of the present invention.

FIG. 6 is a side elevational view of the objects in FIG. 5.

FIG. 18 is a plan view of the objects of FIG. 17, assembled together.

FIG. 19 is a side elevational view of the objects of FIG. 18.

FIG. 20 is a side elevational sectional view of the objects of FIG. 19.

DETAILED DESCRIPTION OF THE PREFERRED EMBODIMENT

Figure 1:
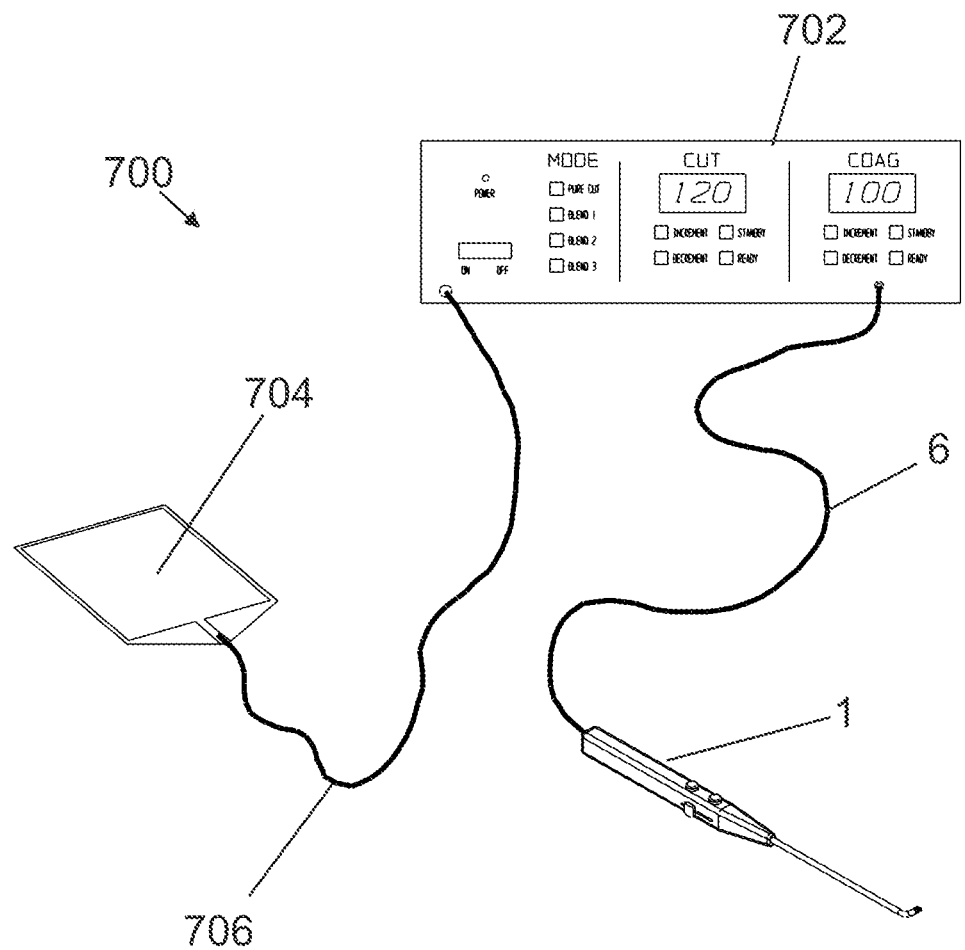
FIG. 1 is a schematic representation of a prior art electrosurgical ablation system.

The present invention constitutes an improvement in the field of electrosurgery, more particularly, an improvement to the safety and reliability of minimally invasive electrosurgical devices adapted for the modification, sculpting, resection, removal, or vaporization of tissue, configured for coagulation, cauterization or hemostasis purposes, or utilized for thermal treatment of normal and tumorous tissues that employ high temperatures to cut, remove or vaporize all or part of a tissue mass.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Elements of the Present Invention

Unless otherwise defined, all technical and scientific terms used herein have the same meaning as commonly understood by one of ordinary skill in the art to which this invention belongs. In case of conflict, the present specification, including following definitions, will control.

The words "a", "an", and "the" as used herein mean "at least one" unless otherwise specifically indicated.

The term "proximal" refers to that end or portion which is situated closest to the user; in other words, the proximal end of an electrosurgical instrument of the instant invention will typically include the handle portion.

The term "distal" refers to that end or portion situated farthest away from the user; in other words, the distal end of an electrosurgical instrument of the instant invention will typically include the active electrode portion.

In certain embodiments, the present invention makes reference to "fluid(s)". As used herein, the term "fluid(s)" refers to liquid(s), either electrically conductive or non-conductive, and to gaseous material, or a combination of liquid(s) and gas(es). In the context of the present invention, the term "fluid" extends to body fluids, examples of which include, but not limited to, blood, peritoneal fluid, lymph fluid, pleural fluid, gastric fluid, bile, and urine.

The present invention makes reference to the vaporization of tissue. As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. The present invention is not limited in terms of the tissue to be treated but rather has broad application, including the resection and/or vaporization any target tissue with particular applicability to the ablation, destruction and removal of problematic joint tissues.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as electrosurgical "probes" or "instruments". The present invention is particularly concerned with the category of electrosurgical devices referred to in the art as "ablators", i.e., electrosurgical electrodes designed primarily for the bulk removal of tissue by vaporization, though the inventive principles extend to electrosurgical device adapted for the cutting of tissue or coagulation of bleeding vessels.

Electrosurgical devices contemplated by the present invention may be fabricated in a variety of sizes and shapes to optimize performance in a particular surgical procedure. For instance, devices configured for use in small joints may be highly miniaturized while those adapted for shoulder, knee and other large joint use may need to be larger to allow high rates of tissue removable. Likewise, electrosurgical devices for use in arthroscopy, otolaryngology and similar fields may be produced with a circular or cylindrical geometry, using turning and machining processes, while such geometries may not be suitable for other applications. Accordingly, the geometry (i.e., profile, perimeter, etc.) may be square, rectangular, polygonal or have an irregular shape to suit a specific need.

The present invention makes reference to one or more "active electrodes" or "active elements". As used herein, the term "active electrode" refers to one or more conductive elements formed from any suitable preferably spark-resistant metal material, such as stainless steel, nickel, titanium, molybdenum, tungsten, and the like as well as combinations thereof, connected, for example via cabling disposed within the elongated proximal portion of the instrument, to a power supply, for example, an externally disposed electrosurgical generator, and capable of generating an electric field. Like the overall electrosurgical device, the size and shape of the active electrode itself and the active surface defined thereby may routinely vary in accordance with the need in the art. It will be understood by those skilled in the art that such choices in geometry constitute a design preference and that other geometries may be used to optimize performance for specific surgical procedures. For example, for accessing narrow structures like vertebral discs it may be desirable to use an elongated electrode of a narrow geometry, e.g., having a relatively flat profile.

The profile, shape and orientation of the exposed electrically active surface(s) of the active electrode may likewise be optimized. The active surface may be elongated and/or contoured, smooth or irregular, with or without grooves or furrows, with or without an array or series of ribs, pins or other protuberance, and may incorporate apertures for the introduction of irrigant to and/or the aspiration of electrosurgery byproducts from the site.

In certain embodiments, the present invention makes reference to one or more "return electrodes". As used herein, the term "return electrode" refers to one or more powered conductive elements to which current flows after passing from the active electrode(s) back to the electrical generator. This return electrode may be located on the ablator device or in close proximity thereto and may be formed from any suitable electrically conductive material, for example a metal material such as stainless steel, nickel, titanium, molybdenum, tungsten, aluminum and the like as well as combinations thereof. Alternatively, one or more return electrodes, referred to in the art as "dispersive pads" or "return pads", may be positioned at a remote site on the patient's body.

In certain embodiments, the present invention makes reference to one or more "floating electrodes" or "floating potential electrodes". As noted above, the employment of "floating electrodes" is described in detail in U.S. Pat. Nos. 7,563,261 and 7,566,333, the contents of which are incorporated by reference herein. Therein, a floating potential electrode is defined as a conductive member that is not connected to any part of the power supply or power supply circuit; as such, the electrical potential of this one or more additional conductive member is not fixed, but rather is "floating" and is determined by size and position of the electrode and the electrical conductivity of the tissue and/or liquid surrounding the distal end of the device. One or more floating electrodes are typically mounted in close proximity to the active electrode and serve to concentrate the power in the vicinity of the active electrode and thereby increase the energy density in the region surrounding the active electrode. Thus, the addition of one or more floating potential electrode(s) substantially modifies the electrical field distribution, and energy deposition, in the vicinity of the active electrode without the possibility of electrode destruction since the floating electrode is not directly connected to the electrical power supply.

The present invention makes reference to an "insulator". As used herein, the term "insulator" refers to the component that surrounds a distal end active electrode, covering all exposed surfaces of the active electrode with the exception of the electrically active surface that generally protrudes beyond the insulator a short distance. Accordingly, the geometry of the insulator is largely dictated by the geometry of the associated active electrode. For example, the use of a substantially circular or cylindrical active electrode dictates the use of a largely tubular insulator sleeve. However, as with the overall electrosurgical device and active electrode itself, the size and shape of the insulator may routinely vary in accordance with the need in the art. It will be understood by those skilled in the art that such choices in geometry constitute a design preference and that other geometries may be used to optimize performance for specific surgical procedures.

The insulator should be fabricated from a suitable electrically non-conductive, biocompatible, preferably ceramic material such as alumina, zirconia, or silicon nitride ceramic.

In the context of the present invention, the word "ceramic" refers to an inorganic, nonmetallic crystalline material prepared by the action of heat and subsequent cooling. The present invention is particularly concerned with "technical ceramics" or "engineering ceramics", which may be classified into three distinct material categories:

(i) oxides such as alumina, beryllia, ceria, zirconia;
(ii) nonoxides such as carbide, boride, nitride, silicide; and
(iii) composites, i.e., reinforced particulates comprising combinations of oxides and nonoxides.

In the context of the prior art, the insulator is typically held in place by an adhesive (typically, an epoxy) and/or by a dielectric coating that covers the elongated distal element of the ablator and overlaps the proximal end of the insulator. The dielectric coating is frequently applied as a powder that is then fused to the device by curing at an elevated temperature. However, in the context of the present invention, the insulator is affixed to the active electrode by means of "brazing" or "brazed joints". As used herein, the term "brazing" refers to a joining process whereby a filler metal (i.e., a "braze alloy") is heated above its melting temperature and distributed between two or more close-fitting parts by capillary action. The filler metal is brought slightly above its melting temperature while protected by a suitable atmosphere, usually a flux. It then flows over the base metal (known as wetting) and is then cooled to join the work pieces together. It is similar to soldering, except the temperatures used to melt the filler metal is above 800° F. (427° C.), more preferably above 842° F. (450° C.).

U.S. Pat. No. 2,667,432 to Nolte describes a method for brazing metals to ceramics using a tightly adhering metal coating. Likewise, U.S. Pat. No. 2,857,663 to Beggs describes ceramic to metal bonding using a foil shim of braze material between the components. A suitable braze alloy having a lower melting point than that of the metal component to be joined is placed between the metal component and the ceramic component. The assembly is heated to a temperature above the melting point of the braze alloy so that the braze material melts, and subsequently adheres to the metal and ceramic components when cooled.

Suitable braze alloys are known in the art and commercially available through Morgan Technical Ceramics (Fairfield, N.J.). Many conventional brazing materials (i.e., "braze alloys") are metal alloys of copper, gold, silver, nickel, chromium, cobalt, molybdenum, platinum, palladium, titanium, silicon, and vanadium. Copper-gold, copper-silver and nickel alloys are particularly common.

Due to their different coefficients of thermal expansion, not all ceramic materials can be brazed to all metal materials. Because brazing is performed in a furnace at high temperatures, when large mismatches in thermal expansion coefficients occur, the braze joint will frequently fail since high stresses are created at the edges of the braze joint due to the difference in the degree of contraction of the materials during cool-down.

Thermal expansion coefficients (in/in-degree F.) of some common materials are listed in Table (1).

TABLE 1

Thermal expansion coefficients of some common materials

| Material | Thermal expansion coefficients (in/in-degree F.) |
|---|---|
| Alumina | 3.0 |
| Austenitic stainless steel (300 series) | 8.0 to 9.5 |
| Ferritic stainless steels (400 series) | 5.5 |
| Titanium | 4.8 |
| Molybdenum | 2.5-3 |

Failure of a braze joint will occur if, during cool-down from the brazing temperature, the difference in the contraction between the metal and ceramic components creates stresses in the braze joint which exceed the shear strength of the braze material, of the braze alloy to ceramic adhesion, or of the ceramic material to which the braze alloy is adhered. The maximum shear stress is determined not only by the coefficients of thermal expansion of the materials joined, but also by the dimensions of the region covered by the braze alloy (braze spot size). At the periphery of the bond, the shear stress will be generally proportional to the distance across the bond if the bond is on an uninterrupted planar surface. Somewhat larger bonds may be formed without failure if the bond surface is not continuous but rather contains voids that do not contribute to the shear stress across the void.

Accordingly, successful brazing of a ceramic and metal component requires that the coefficients of the ceramic component and the metal component be closely matched and that the stresses causes by any mismatch in the coefficients not exceed the shear strength of the ceramic, of the ceramic/braze bond, or of the braze material. For an electrosurgical ablator having an alumina insulator, one preferred active electrode material is 400 series stainless steel because of the similarity in coefficients of thermal expansion, but other metals having a greater resistance to spark erosion may be successfully used. In the context of the present invention, the coefficient of thermal expansion of a selected metal electrode material ($\alpha_E$) is preferably more than half (0.5×) and less than twice (2×) the coefficient of thermal expansion of a selected non-conductive insulator material ($\alpha_I$).

As noted above, Morgan Technical Ceramics (New Bedford, Mass.) produces a variety of materials, many of which are suitable for medical devices. Examples of such suitable biocompatible brazing materials are metals and metal alloys that include nickel, cobalt, chromium, molybdenum, titanium, silicon, and the like.

Stress on a brazed bond arising from thermal coefficient mismatch can be decreased by decreasing the deposition area or "braze area". Because the bond strength of the brazed joint is high, the braze area required to meet design requirements is small. In the context of the instant invention, the braze area may simply be a single deposition or "braze spot" or, alternatively may be made up of a number of contiguous or discontiguous braze spots. Although the examples described below make reference to round depositions, braze spots of other shapes are contemplated herein and may be used depending on the particular design constraints. For instance, to fit within the bounds of certain components or assemblies, the deposition of braze alloy, or "braze spot", may need to be square, rectangular, ellipsoid, or alternatively may have an irregular linear/curvilinear perimeter.

The present invention relates to the discovery that braze area(s) on the order of 7 mm$^2$ or less, preferably 4 mm$^2$ or less, more preferably on the order of 1.5-2.0 mm$^2$ or less, are sufficient to successfully bond active electrodes to insulators and produce assembled, compact electrosurgical devices suited for many demanding medical applications. If the braze alloy spot is round, it preferably has a diameter of on the order of 3 mm or less, and more preferably on the order of 1.5 mm or less (i.e., a deposition area of about 7 mm$^2$ or less, more preferably of about 1.8 mm$^2$ or less). If an alternate braze spot shape is selected, the maximum width should be minimized, with the area of the braze spot being determined by the strength requirement of the finished brazed joint and the methods for depositing the braze alloy into the joint at assembly. In cases in which the braze spot is contiguous, it is preferable that the maximum width be 3 mm or less, more preferably 1.5 mm or less. For example, for alumina cylindrical insulators having outside diameters up to 4 millimeters and wall thicknesses between 0.3 and 0.8 millimeters, the proximal end surface may be bonded to a 400 series or similar active electrode, such that the maximum shear stresses in the brazed joint is less than the maximum shear strength of the ceramic, braze material or ceramic/braze bond.

Utilities of the Present Invention

As noted above, the present invention is directed to compact, safe and reliable electrosurgical devices adapted for the modification, sculpting, resection, removal, or vaporization of tissue, configured for coagulation, cauterization or hemostasis purposes, or utilized for thermal tissue treatment, particularly those that employ high temperatures to cut, remove or vaporize all or part of a soft tissue or tumor mass, such devices having particular utility in the context of arthroscopy and the removal of problematic joint tissues. However, as noted previously, the present invention is not restricted thereto. Aspects are equally applicable to other uses, for example in connection with reconstructive, cosmetic, oncological, ENT, urological, gynecological, and laparascopic procedures, as well as in the context of general open surgery.

While some embodiments of the present invention are designed to operate in dry or semi-dry environments, others utilize the endogenous fluid of a "wet field" environment to transmit current to target sites. Still others require the use of an exogenous irrigant. In certain embodiments, the "irrigant" (whether native or externally applied) is heated to the boiling point, whereby thermal tissue treatment arises through direct contact with either the boiling liquid itself or steam associated therewith. This thermal treatment may include desiccation to stop bleeding (hemostasis), and/or shrinking, denaturing, or enclosing of tissues for the purpose of volumetric reduction (as in the soft palate to reduce snoring) or to prevent aberrant growth of tissue, for instance, endometrial tissue or malignant tumors.

Liquids (either electrically conductive or non-conductive) and gaseous irrigants, either singly or in combination may also be advantageously applied to devices for incremental vaporization of tissue. Normal saline solution may be used. Alternatively, the use of low-conductivity irrigants such as water or gaseous irrigants or a combination of the two allows increased control of the electrosurgical environment.

The electrosurgical devices of the present invention may be used in conjunction with existing diagnostic and imaging technologies, for example imaging systems including, but not limited to, MRI, CT, PET, x-ray, fluoroscopic, thermographic, photo-acoustic, ultrasonic and gamma camera and ultrasound systems. Such imaging technology may be used to monitor the introduction and operation of the instruments of the present invention. For example, existing imaging systems may be used to determine location of target tissue, to confirm accuracy of instrument positioning, to assess the degree of tissue vaporization (e.g., sufficiency of tissue removal), to determine if subsequent procedures are required (e.g., thermal treatment such as coagulation and/or cauterization of tissue adjacent to the target tissue and/or surgical site), and to assist in the traumatic removal of the device.

As noted above, the electrosurgical instruments of the present invention find utility in treatment of soft tissue. Brazed joints can withstand high temperatures without the problem of insulator failure and ejection associated with prior art devices. Accordingly, the present invention is not particularly limited to the treatment of any one specific disease, body part or organ or the removal of any one specific type of tissue, the components and instruments of the present invention.

Illustrative Embodiments of the Present Invention

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

As noted above, the present invention provides a marked improvement to the safety and reliability of minimally invasive electrosurgical devices and methods through its employ of brazed joints. Electrosurgical devices, such as ablators, that use brazing to join electrodes to ceramic insulators operate in the same manner as other devices, but are substantially more compact and rugged. Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

FIG. 1 depicts a conventional electrosurgical system suitable for use with an ablator formed in accordance with the principles of this invention. Referring to FIG. 1, electrosurgical system 700 includes an electrosurgical power supply 702, an electrosurgical ablator 1 with electrical cord 6, and a dispersive (return) electrode 704 with electrical cord 706.

Figure 2:
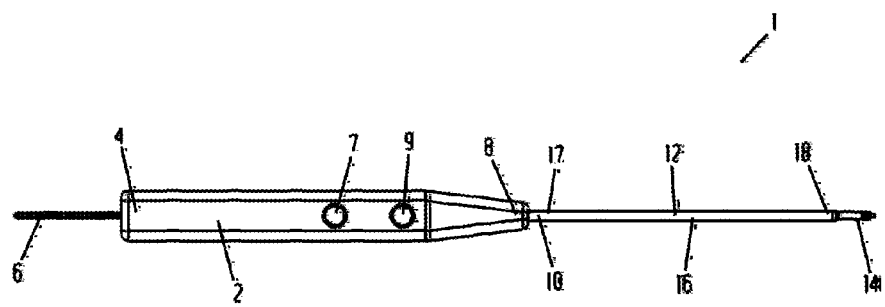
FIG. 2 is a plan view of the electrosurgical ablator depicted in FIG. 1.
Figure 3:
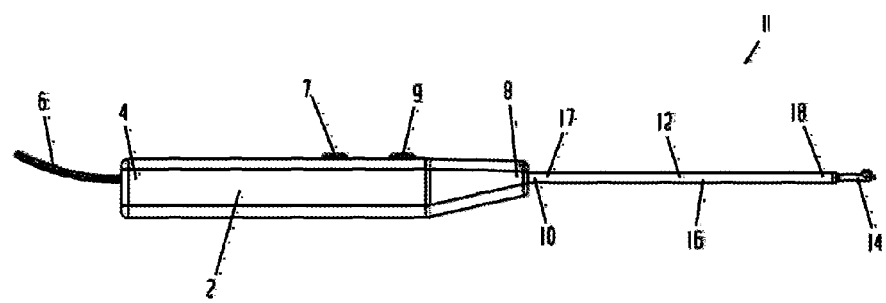
FIG. 3 is a side elevational view of the electrosurgical ablator depicted in FIG. 1.
Figure 4:
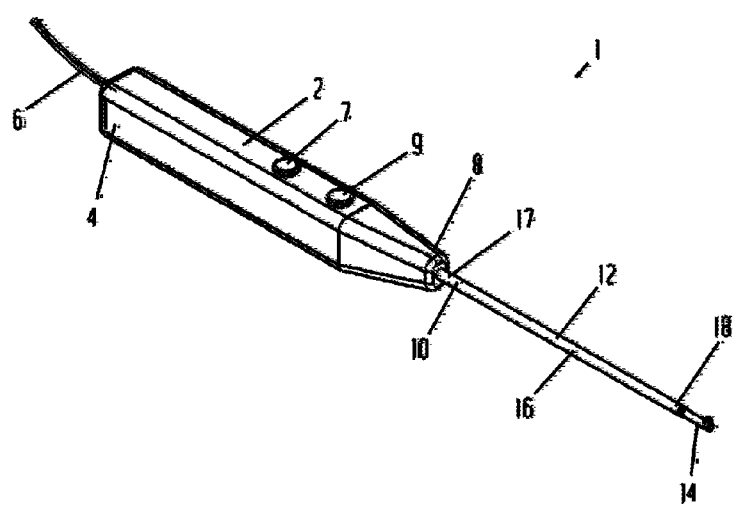
FIG. 4 is a perspective view of the electrosurgical ablator depicted in FIG. 1.
Figure 8:
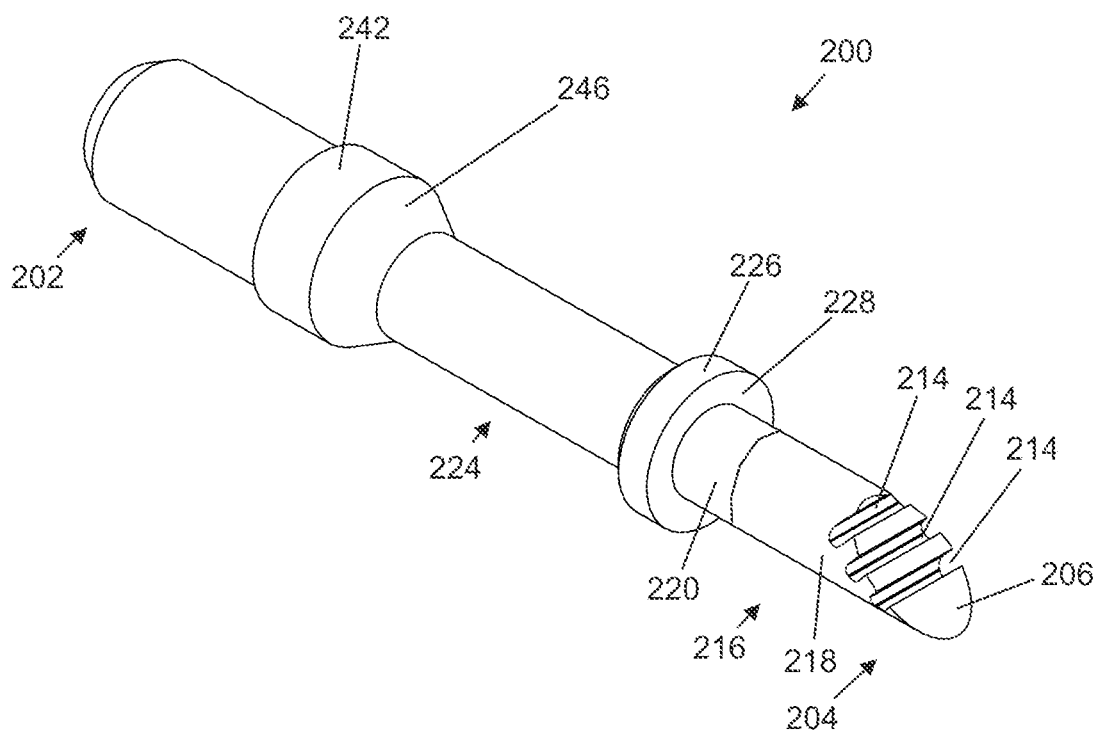
FIG. 8 is a perspective view of the objects of FIG. 5.
Figure 7:
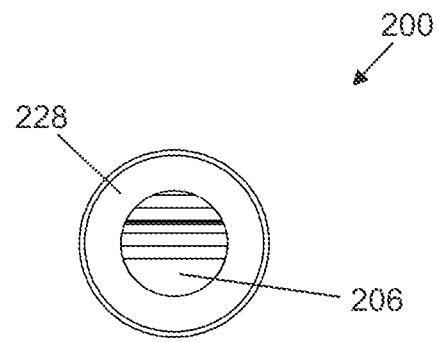
FIG. 7 is a distal end view of the objects of FIG. 5.
Figure 11:
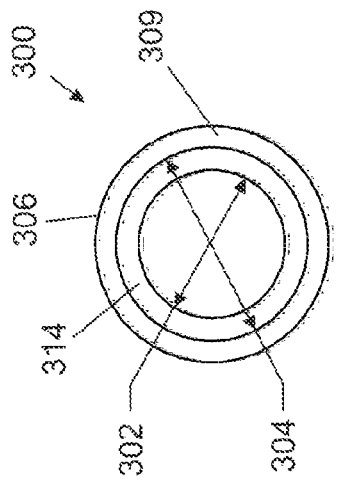
FIG. 11 is a distal end view of the objects of FIG. 9.
Figure 12:
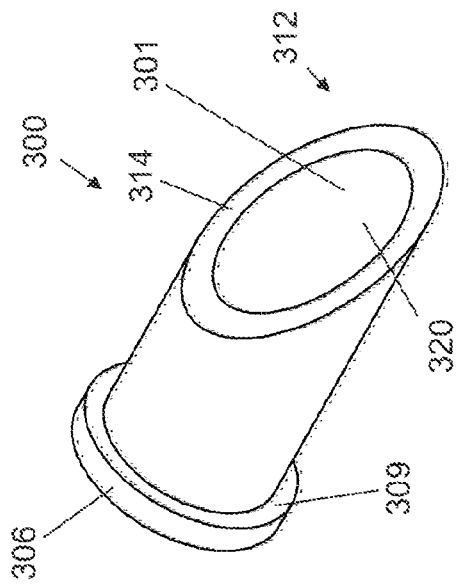
FIG. 12 is a perspective view of the objects of FIG. 9.
Figure 9:
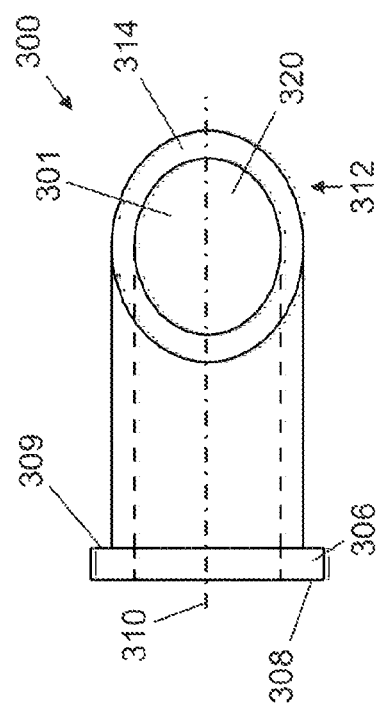
FIG. 9 is a plan view of an insulator for an electrosurgical ablator formed in accordance with the principles of this invention.
Figure 10:
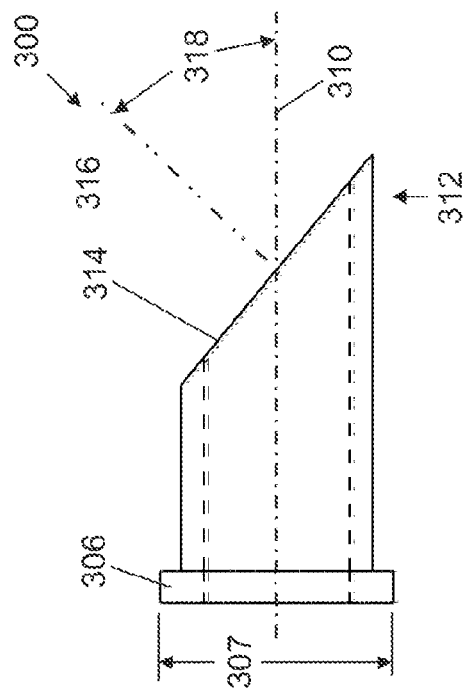
FIG. 10 is a side elevational view of the objects of FIG. 9.
Figure 16:
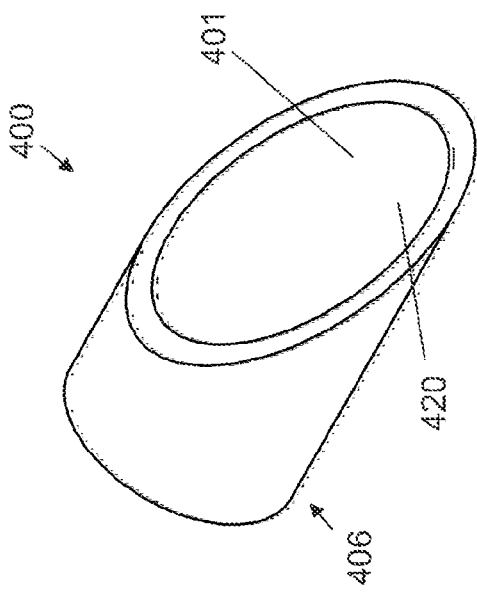
FIG. 16 is a perspective view of the objects of FIG. 13.
Figure 15:
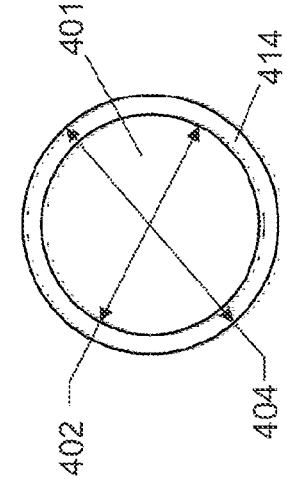
FIG. 15 is a distal end view of the objects of FIG. 13.
Figure 13:
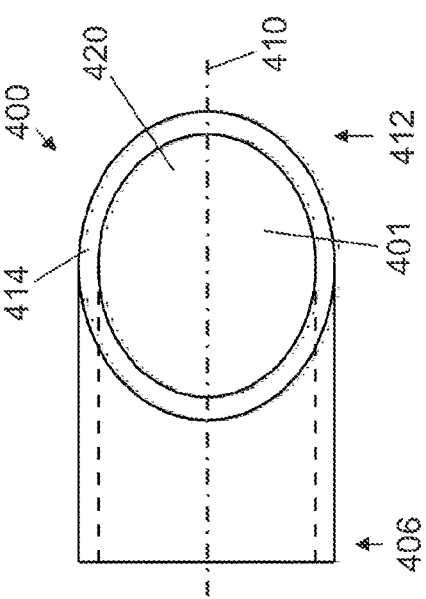
FIG. 13 is a plan view of a floating electrode for an electrosurgical ablator formed in accordance with the principles of this invention.
Figure 14:
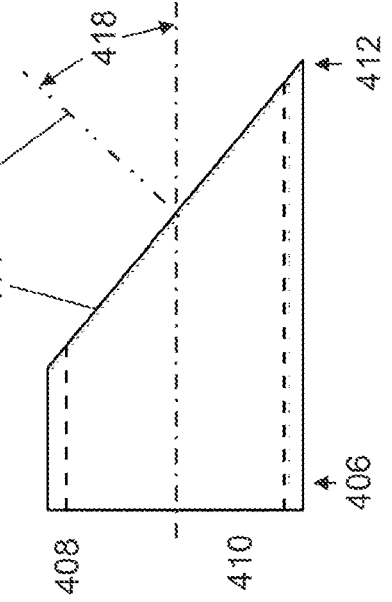
FIG. 14 is a side elevational view of the objects of FIG. 13.
Figure 17:
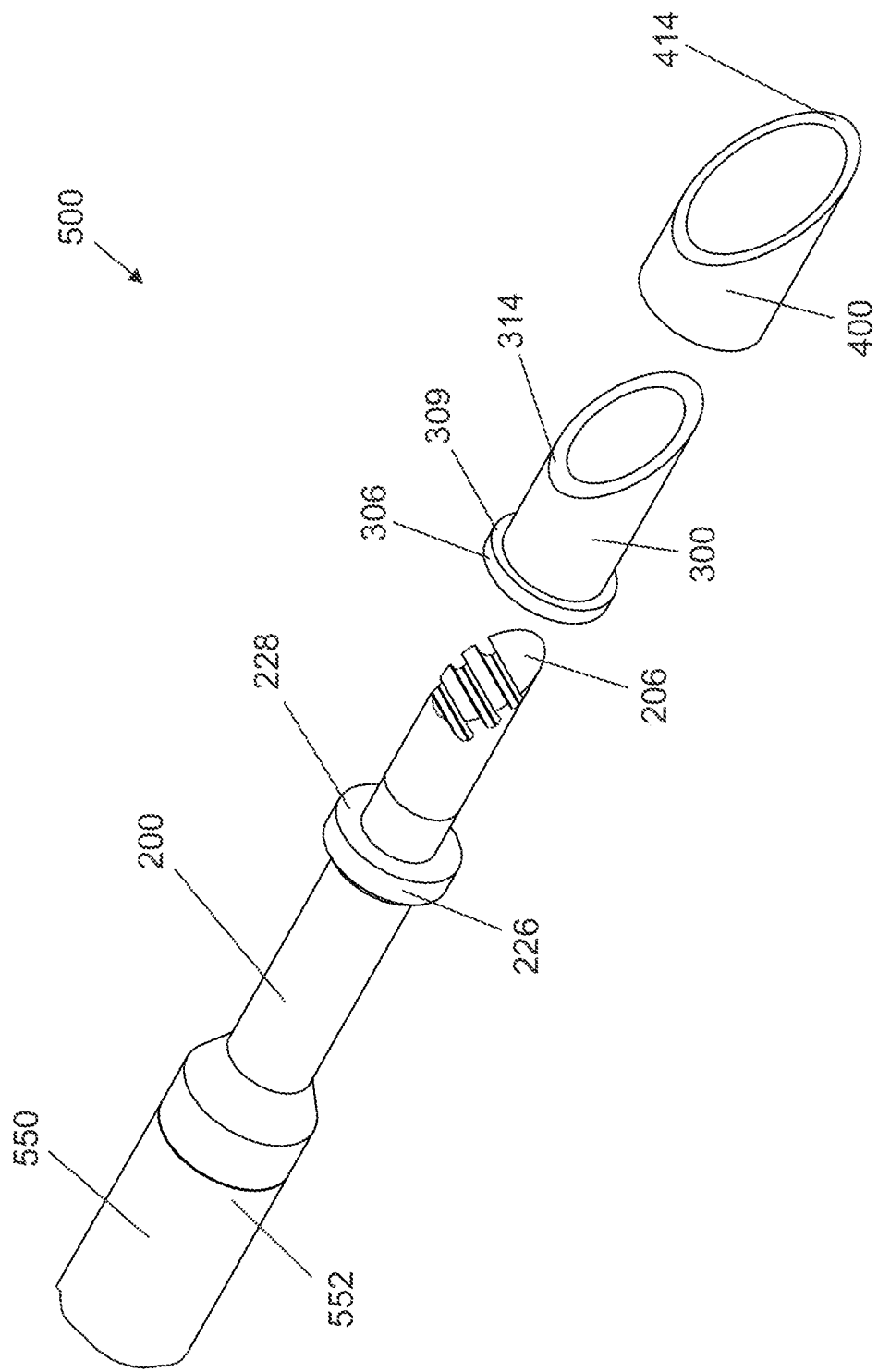
FIG. 17 is an exploded perspective view of the components that make up the distal end of an ablator formed in accordance with the principles of this invention.
Figure 21:
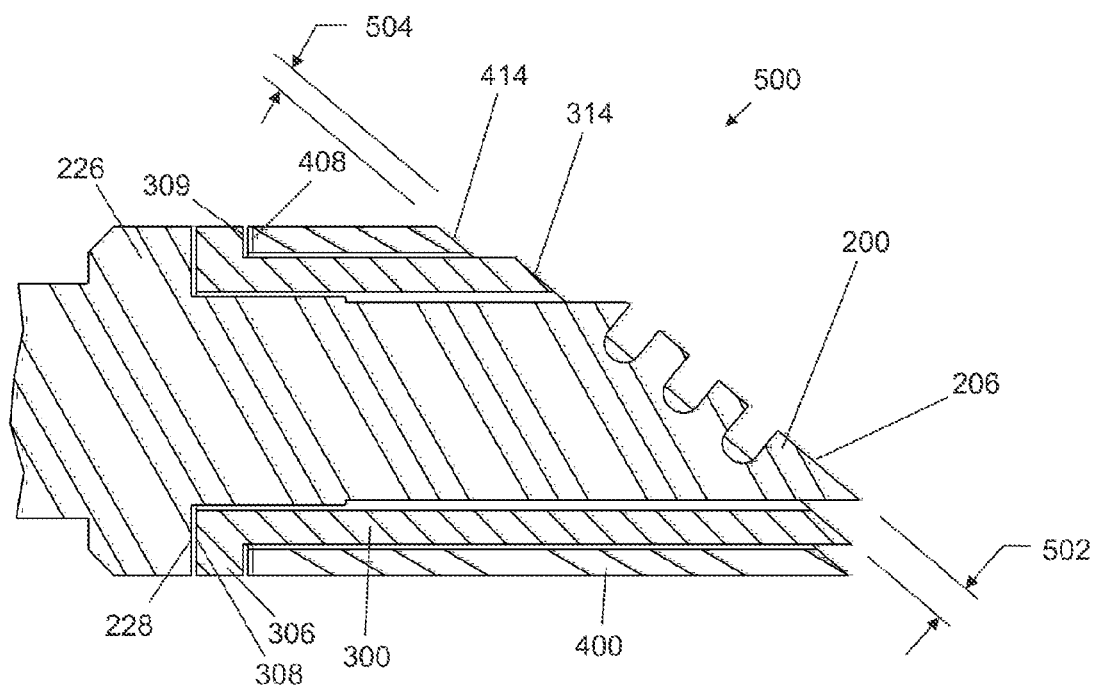
FIG. 21 is an expanded view of the distal end objects of FIG. 20.
Figure 22:
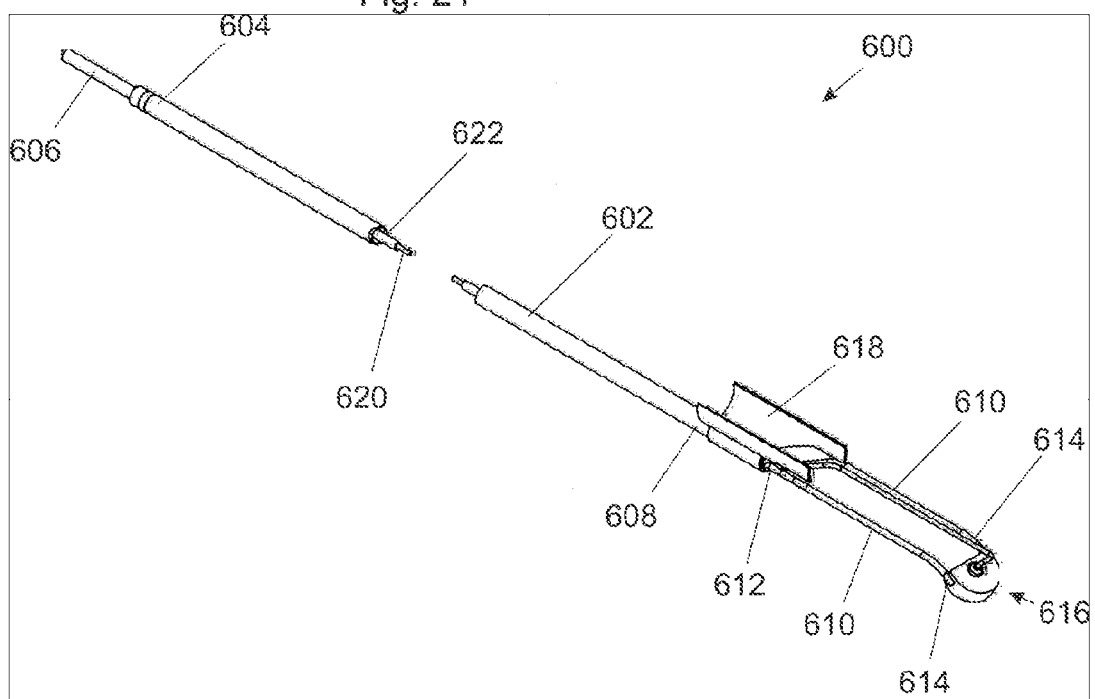
FIG. 22 is a perspective view of an electrosurgical ablator formed in accordance with the principles invention, configured for use with a resectoscope.
Figure 23:
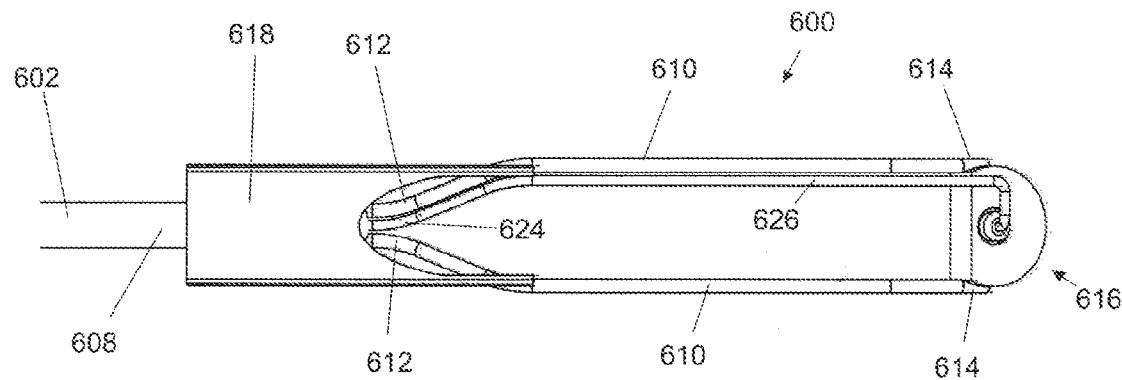
FIG. 23 is a plan view from above of the objects of FIG. 22.
Figure 24:
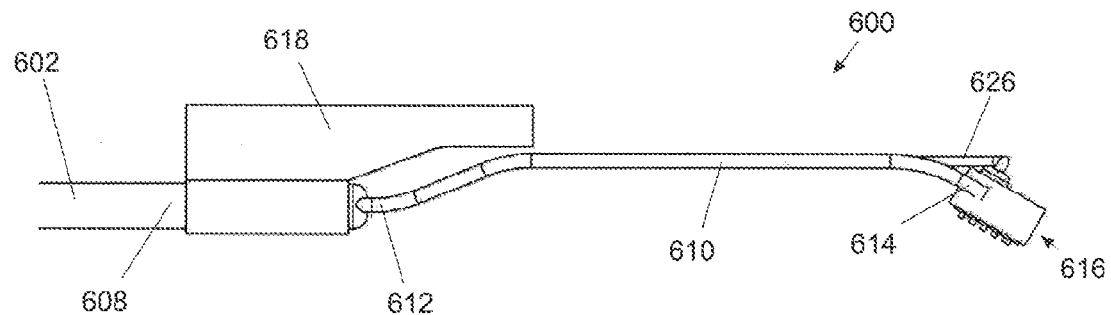
FIG. 24 is a side elevational view of the objects of FIG. 22.
Figure 25:
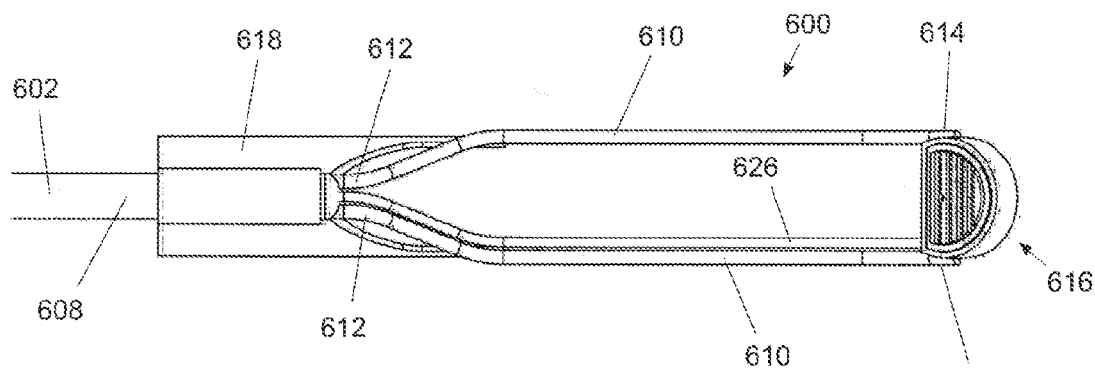
FIG. 25 is a plan view from below of the objects of FIG. 22.
Figure 26:
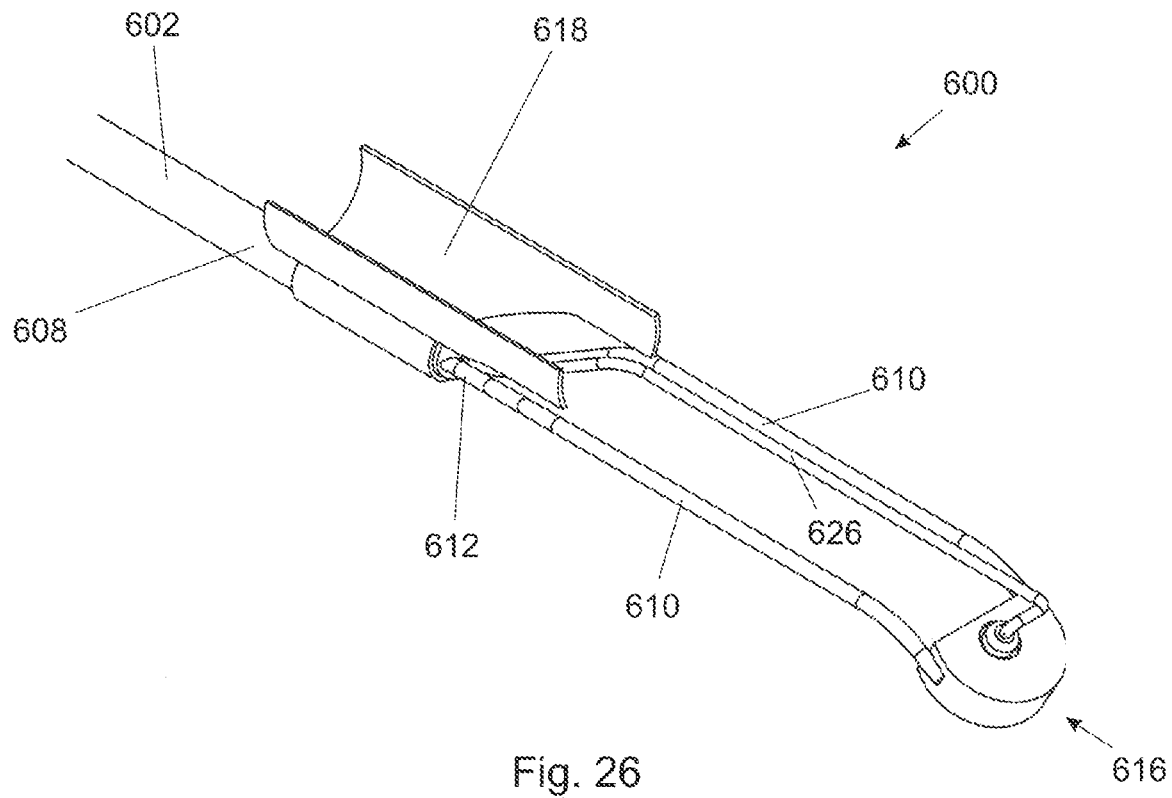
FIG. 26 is an expanded view of the distal end objects of FIG. 22.
Figure 27:
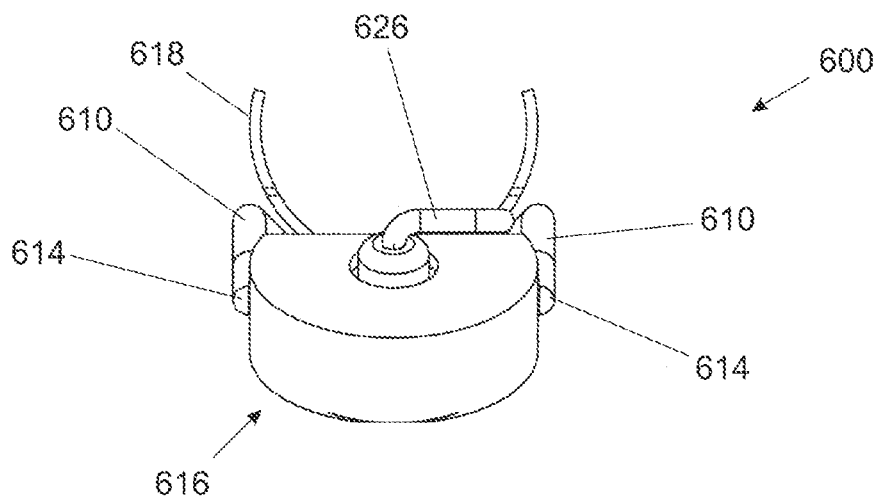
FIG. 27 is a plan view from the distal perspective of the objects of FIG. 26.

FIGS. 2 through 4 depict the details of electrosurgical ablator 1 of FIG. 1. Electrosurgical ablator 1 has a proximal portion 2 forming a handle and having a proximal end 4 from which passes electrical cord 6, and a distal end 8 which attaches to proximal end 10 of elongated distal portion 12. Electrosurgical ablator 1 also has a distal portion 12 composed of a distal end element 14 (active electrode) and a tubular portion 16. Tubular portion 16 has a proximal end 17 and a distal end 18. Buttons 7 and 9 control the power (typically RF power) applied to the device.

FIGS. 5 through 8 depict the details of active electrode 200 formed in accordance with the principles of this invention. Active electrode 200 is analogous to distal end element 14 of the electrosurgical ablator 1 of FIGS. 2 through 4 and includes a proximal end 202 configured for mounting to the distal end of a tube, for example the proximal portion of an electrosurgical ablator. Distal end 204 has an ablating surface 206 formed thereon. Dotted line 208 is normal to ablating surface 206 and forms an angle 210 with longitudinal axis 212 of electrode 200. Ablating surface 206 has grooves 214 formed therein. Portion 219 of element 200 has a diameter of 221. Middle portion 224 of electrode 200 has flange 226 at its distal end, wherein flange 226 has a distal surface 228 perpendicular to axis 212, a conical proximal surface 230. The proximal end 240 of middle portion 224 has formed thereon a flange 242 having a proximal planar surface 244 to which axis 212 is normal, and a conical distal surface 246. Electrode 200 is formed from a metal having a coefficient of thermal expansion approximating that of alumina. In a preferred embodiment, electrode 200 is formed from a 400 series stainless steel. It will be understood by those skilled in the art that certain aspects of active electrode 200 may be modified or eliminated to suit certain design requirements. For instance, on miniaturized devices middle portion 224 may be eliminated such that such that flange 228 is combined with flange 242 with distal surface 228 at its distal end.

FIGS. 9 through 12 depict an insulator for an electrosurgical ablator formed in accordance with the principles of this invention. Insulator 300, formed from a suitable dielectric material such as, for instance, alumina or other ceramic material, is tubular in form having a lumen 301 with a diameter 302 slightly larger than diameter 221 of portion 219 of active electrode 200, and an outside diameter 304. Insulator 300 has a proximal end flange 306 with a planar proximal face 308 and a planar distal face 309, both having normal lines parallel to axis 310 of insulator 300. Flange 306 has an outside diameter 307 approximately equal to diameter 227 of flange 226 of element 200. Insulator 300 has a distal end 312 that forms a planar surface 314 having a normal line 316 angularly displaced from longitudinal axis 310 at angle 318, angle 318 being approximately equal to angle 210 of element 200. Lumen 301 intersects surface 314 to form distal opening 320.

FIGS. 13 through 16 depict a floating electrode for an electrosurgical ablator formed in accordance with the principles of this invention. Floating electrode 400, formed from a suitable metal material such as, for instance, a 400 series stainless steel or one having a suitable coefficient of thermal expansion and sufficient resistance to spark erosion, is tubular in form having a lumen 401 with a diameter 402 slightly larger than diameter 304 of insulator 300, and an outside diameter 404 approximately equal to diameter 307 of flange 336 of insulator 300. Floating electrode 400 has a proximal face 408 having a normal parallel to axis 410 of electrode 400. Insulator 400 has a distal end 412 forming a planar surface 414 having a normal line 416 angularly displaced from longitudinal axis 410 at angle 418, angle 418 being approximately equal to angle 310 of insulator 300. Lumen 401 intersects surface 414 to form distal opening 420.

FIGS. 17 through 21 depict a distal assembly 500 for an ablator formed in accordance with the principles of this invention. Floating electrode 400 is coaxially assembled to insulator 300 and affixed thereto by a brazed joint formed between proximal surface 408 of electrode 400 and distal surface 309 of flange 306 of insulator 300. Insulator 300 and electrode 400 affixed thereto are coaxially assembled to distal end element (active electrode) 200 and affixed thereto by a brazed joint formed between proximal face 308 of flange 306 of insulator 300 and distal surface 228 of flange 226 of active electrode 200. The proximal end 202 of element 200 is assembled to distal end 552 of tube 550. Surface 206 of active electrode 200 protrudes beyond surface 314 of insulator 300 distance 502 and is parallel thereto. Surface 314 of insulator 300 protrudes beyond surface 414 of floating electrode 400 distance 504 and is parallel thereto. The electrode assembly 500 shown in FIG. 17 has a circular or cylindrical geometry. However, as noted above, those skilled in the art will understand that the choice of the geometry is a design preference and that other geometries may be used to optimize performance for specific surgical procedures.

The operation of an ablator having a floating electrode is described in detail in U.S. Pat. No. 7,563,261 to Carmel et al. Ablator 1 with brazed distal assembly 500 differs in operation from that in the Carmel patent only in its ability to withstand higher operating temperatures without thermal failure. The benefit is equally great when second (floating) electrode 400 is electrically connected to the electrosurgical generator so as to function as a return electrode, or when second (floating) electrode 400 is eliminated so as to form a conventional (active electrode only) ablator. In all cases the device may be operated at higher temperatures without failure due to the high temperature capability of the brazed joints, and the higher temperature capability of the heat-shrink polymeric insulation used to insulate the distal portion of the device compared to the powder-coat insulations currently in use. If thermal/electrical failure of the polymeric insulation occurs the insulator and/or second electrode will not be ejected into the patient because the brazed joint will not fail.

FIGS. 22 through 30 depict an alternate embodiment of the invention herein disclosed configured for use with a resectoscope. Probe 600 has an elongated tubular member 602 with a proximal end 604 having an electrical connector 606 suitable for connecting via an electrical cable to an electrosurgical generator, and a distal end 608. Members 610 have proximal ends 612 mounted to distal end 608 of elongated tubular member 602, and distal ends 614 to which are mounted electrode assembly 616. Electrode stabilizer 618 for stabilizing the distal end of probe 600 is proximate to a distal region of a telescope mounted in a resectoscope working element. Conductive member 620 covered by insulation 622 extends from electrical connector 606 to proximal end 624 of insulated conductive member 626.

Figure 28:
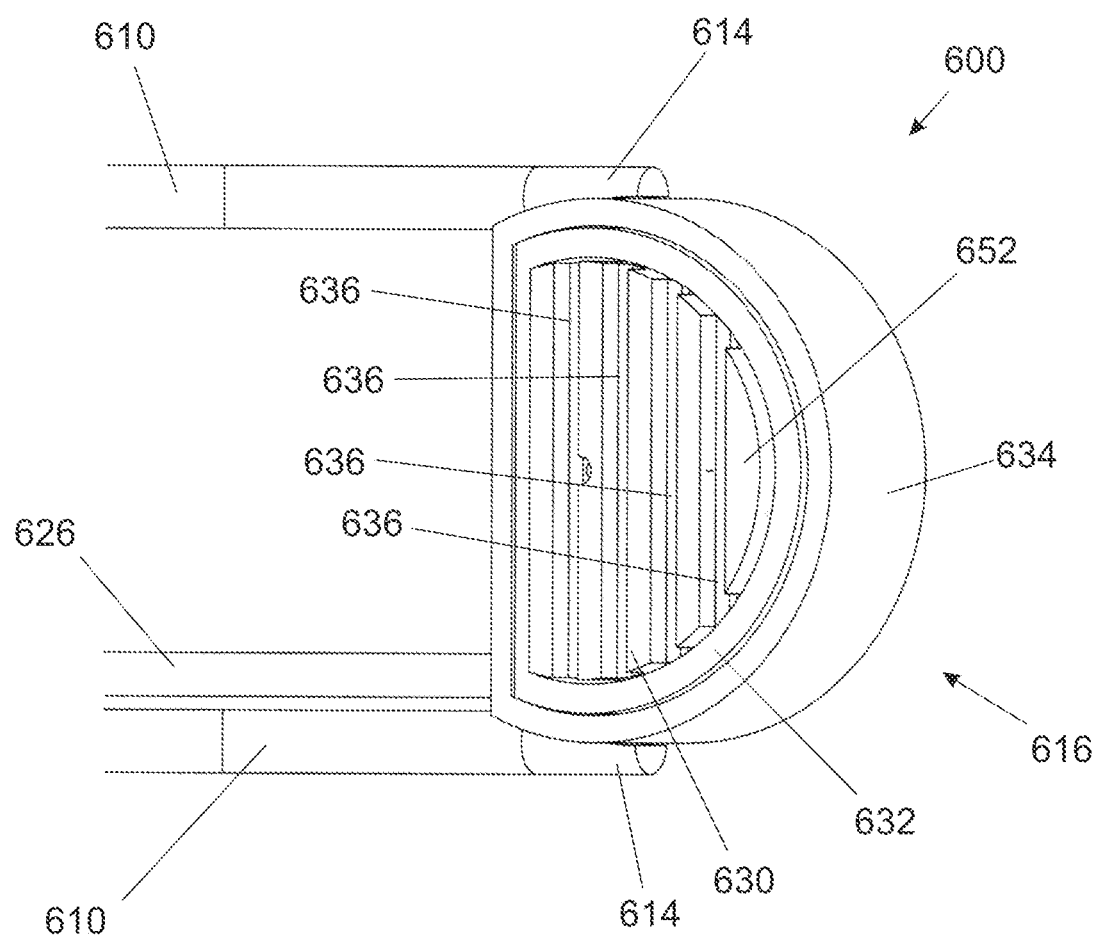
FIG. 28 is an expanded view of the distal end of the objects of FIG. 25.
Figure 29:
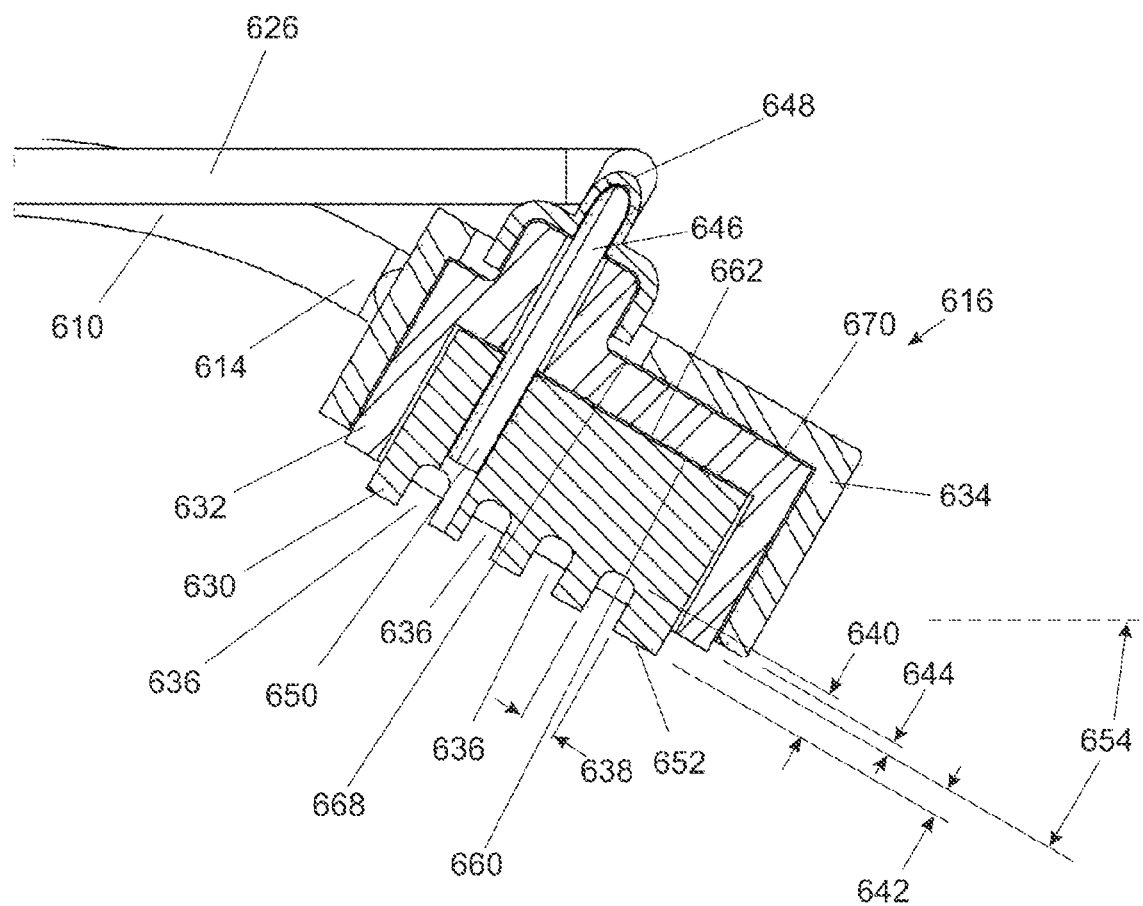
FIG. 29 is a side elevational sectional view of the distal end objects of FIG. 24.

Referring now to FIGS. 28 and 29 depicting the distal-most portion of probe 600, electrode assembly 616 includes active electrode 630, insulator 632 and floating electrode 634. Active electrode 630 has a plurality of grooves 636 of width 638 and depth 640, width 638 and depth 640 being selected to trap bubbles in the grooves. Active electrode 630 is formed from a suitable metal material, such as stainless steel, nickel, titanium or tungsten. Insulator 632 is formed from a suitable dielectric material such as alumina or zirconia. Floating electrode 634 is formed from a suitable metal material, such as stainless steel, nickel, titanium or tungsten. Active electrode 630 protrudes beyond insulator 632 distance 642. Insulator 632 protrudes beyond floating electrode 634 distance 644. Insulated conductive member 626 has a conductive portion 646 coated with dielectric material 648. Distal end 650 portion 646 is connected to active electrode 630. Active electrode 632 has surface 652 segmented by grooves 636. Surface 636 forms an acute angle 654 with the axis of tubular member 602.

Figure 30:
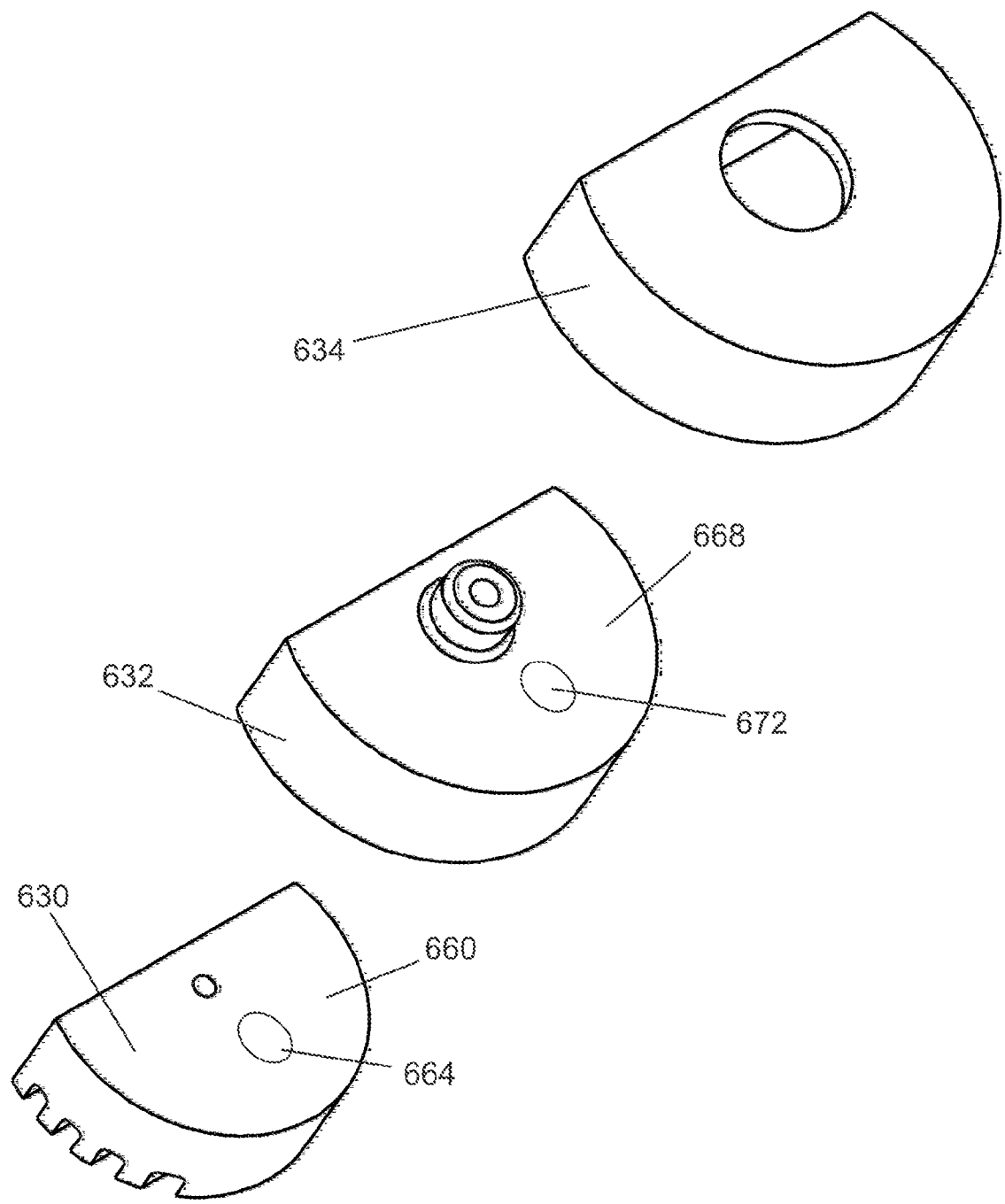
FIG. 30 is an exploded perspective view of the objects that make up the objects of FIG. 27.
Figure 31:
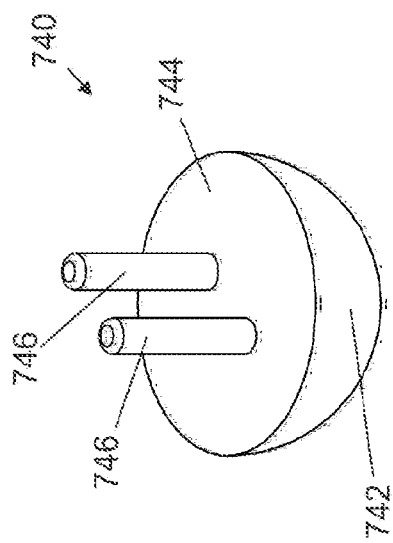
FIG. 31 is a plan view of an alternate active electrode formed in accordance with the principles of the present invention.
Figure 32:
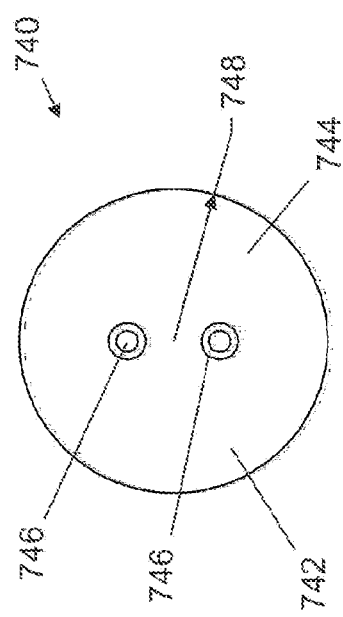
FIG. 32 is a front elevational view of the objects of FIG. 31.
Figure 34:
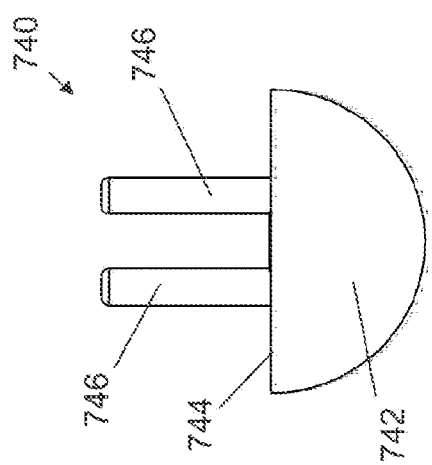
FIG. 34 is a perspective view of the objects of FIG. 31.
Figure 33:
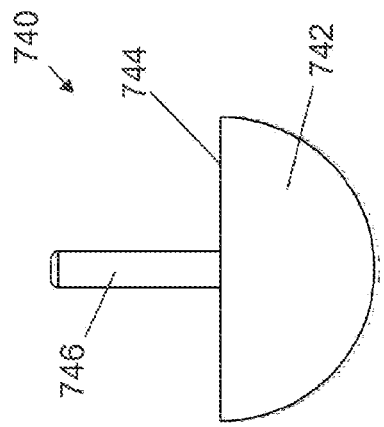
FIG. 33 is a side elevational view of the objects of FIG. 31.
Figure 38:
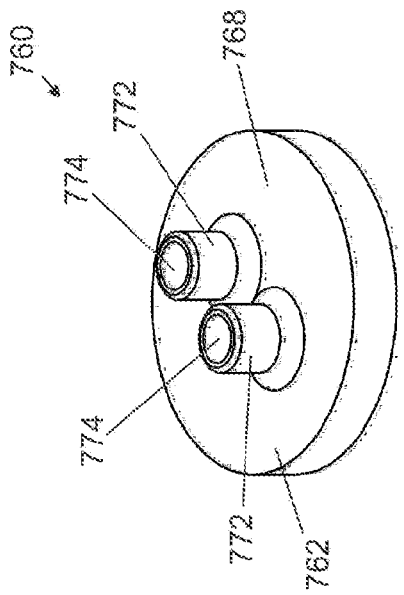
FIG. 38 is a perspective view of the objects of FIG. 35.
Figure 37:
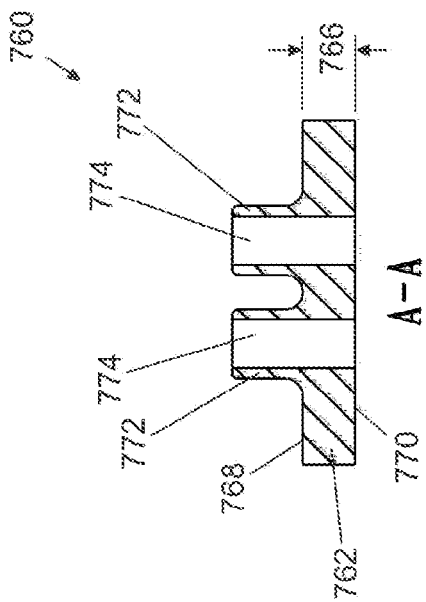
FIG. 37 is a sectional view of the objects of FIG. 36.
Figure 35:
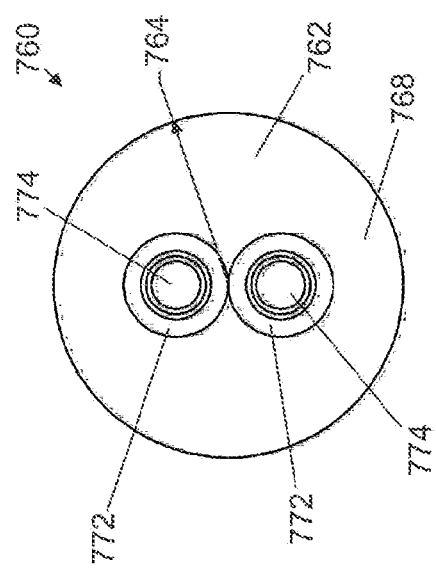
FIG. 35 is a plan view of an alternate insulator formed in accordance with the principles of the present invention, suited for use in combination with the active electrode of FIGS. 31-34.
Figure 36:
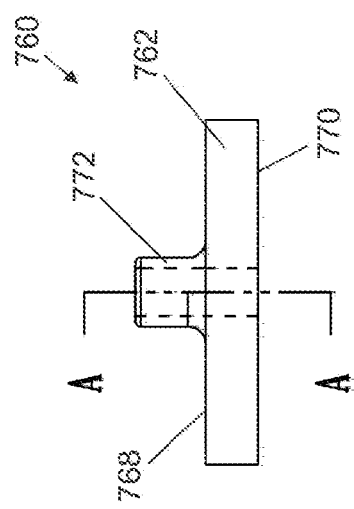
FIG. 36 is a front elevational view of the objects of FIG. 35.

Surface 660 of active electrode 630 is affixed to surface 662 of insulator 632 by a brazed joint formed by braze alloy 664 placed therebetween as depicted in FIG. 30. Surface 668 of insulator 632 is affixed to surface 670 of electrode 634 by a brazed joint formed by braze alloy 672 placed therebetween as depicted in FIG. 30. Braze alloy 664 is depicted as a single round deposition. However, as noted above, those skilled in the art will readily recognize that the quantity, size and shape of the braze alloy depositions or "braze spots" may be routinely varied in accordance with desired design constraints. As with the previous embodiment, second electrode 634 is depicted and described as a floating electrode unconnected to the power supply. However, the benefits of this invention are the equally realized when second electrode 634 is connected to the power supply so as to serve as a return electrode, or when electrode 634 is eliminated so as to make ablator 600 a conventional monopolar ablator.

FIGS. 31 through 34 depict an active electrode 740 for an alternate embodiment of the invention herein disclosed. Electrode 740 has a hemispherical portion 742 of radius 748 with a planar upper surface 744 from which protrude cylindrical portions 746. In a preferred embodiment portions 746 are integral with hemispherical portion 742. In other embodiments portions 746 are cylindrical elements inserted into holes in hemispherical portion 742 and welded in place.

FIGS. 35 through 38 depict an insulator 760 for use with the alternate embodiment active electrode 740. Insulator 760 has a cylindrical portion 762 of radius 764 equal to radius 748 of active electrode 740, and height 766. Cylindrical portion 762 has a top surface 768 and a bottom surface 770. Protruding from top surface 768 tubular portions 772 have lumens 774 which extend through cylindrical portion 762, the size and spacing of lumens 774 being configured to receive cylindrical portions 746 of active electrode 740 as shown in FIG. 39.

Figure 39:
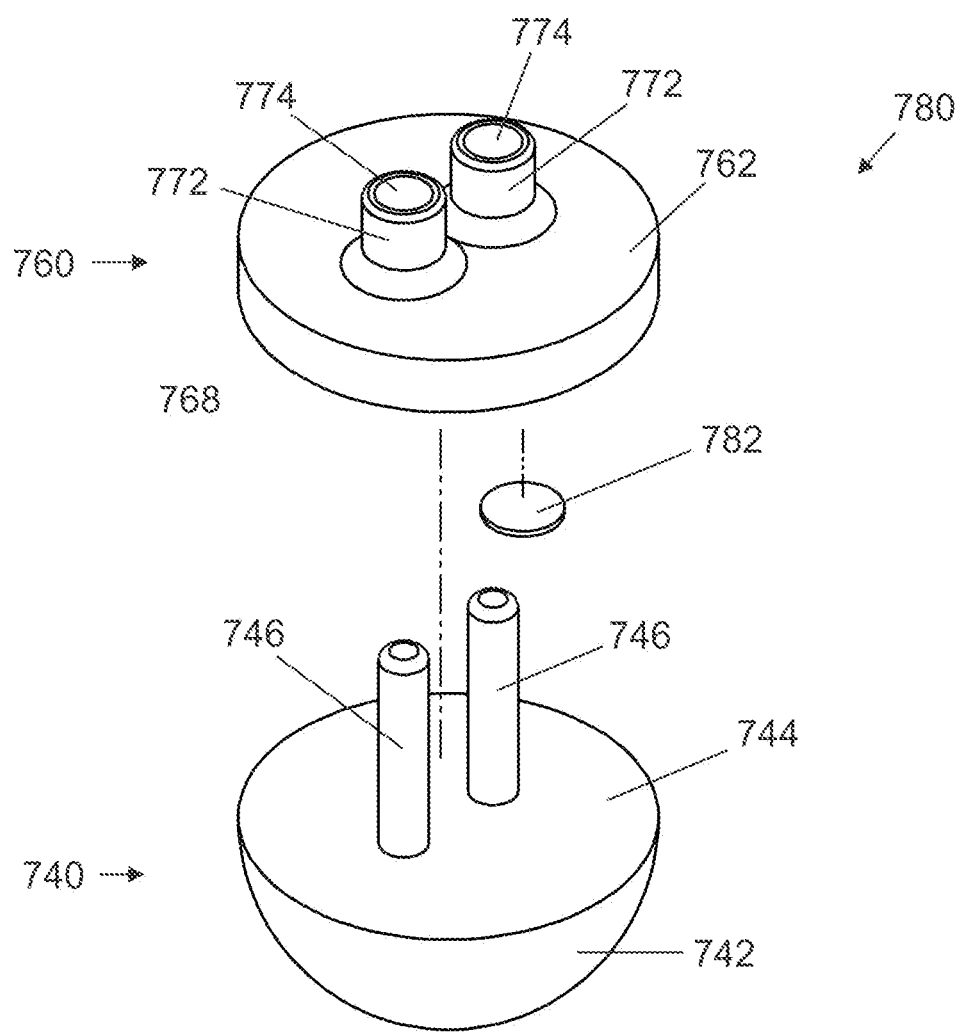
FIG. 39 is an exploded view of an assembly of the objects of FIG. 31 and FIG. 35.
Figure 40:
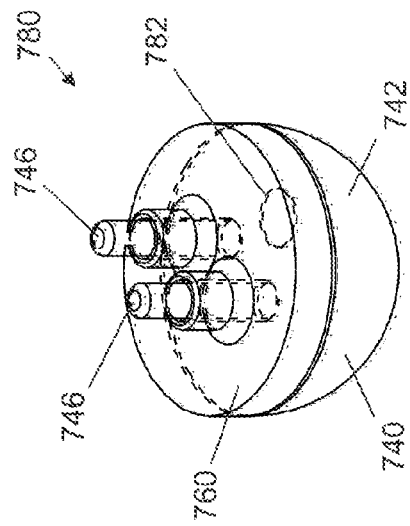
FIG. 40 is a plan view of an assembly of objects of FIG. 31 and FIG. 35.
Figure 41:
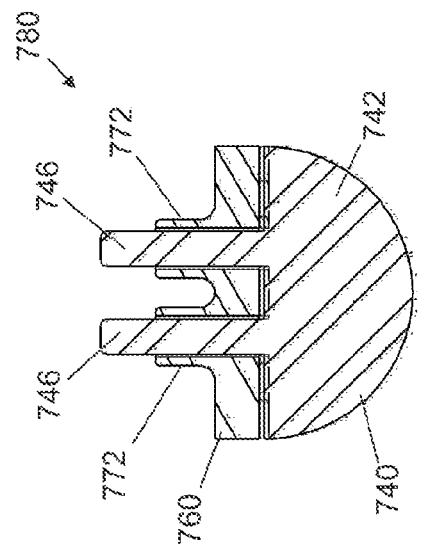
FIG. 41 is a front elevational view of the objects of FIG. 40.
Figure 43:
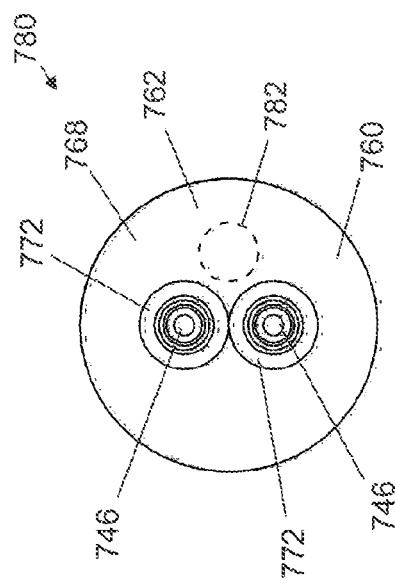
FIG. 43 is a perspective view of the objects of FIG. 40.
Figure 42:
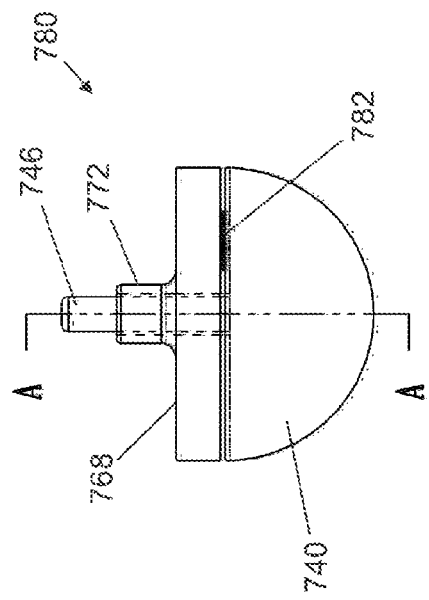
FIG. 42 is a sectional view of the objects of FIG. 41.
Figure 47:
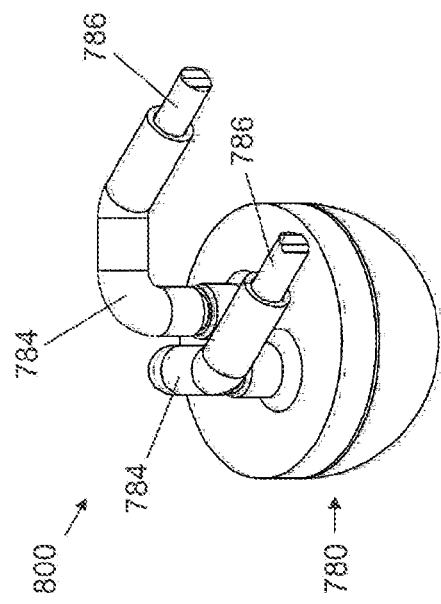
FIG. 47 is a perspective view of the objects of FIG. 44.
Figure 46:
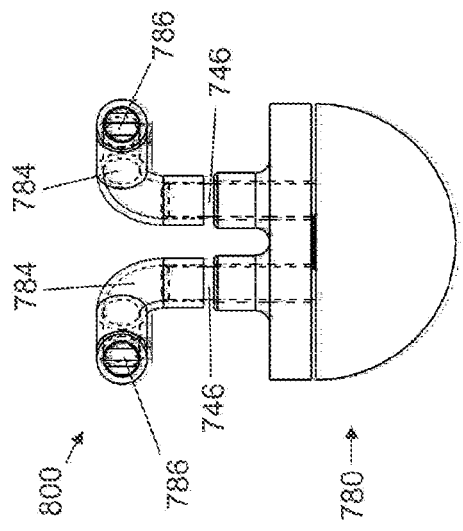
FIG. 46 is a side elevational view of the objects of FIG. 44.
Figure 44:
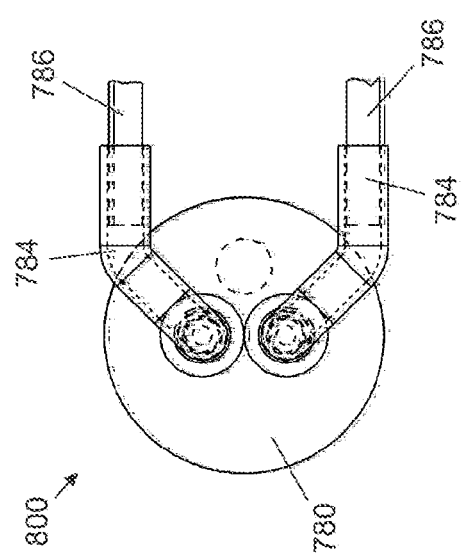
FIG. 44 is a plan view of the assembly of FIG. 40 configured for use with a resectoscope.
Figure 45:
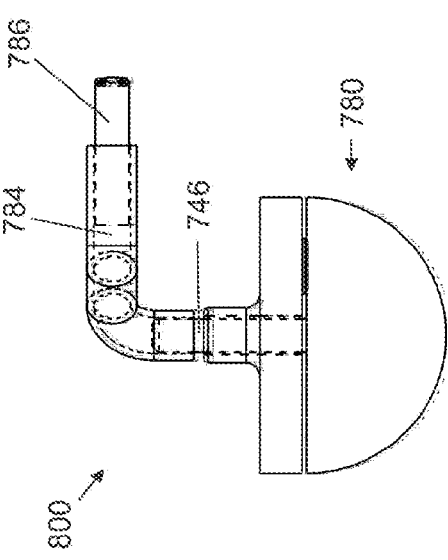
FIG. 45 is a front elevational view of the objects of FIG. 44.

Referring to FIG. 39, electrode 740 and insulator 760 when assembled to form assembly 780 (FIGS. 40 through 43) have braze material element 782 positioned between top bottom surface 770 of insulator 760 and upper surface 744 of insulator 740. Braze material 782, when assembly 780 is heated in a furnace through a predetermined thermal cycle, adheres to surface 770 of insulator 760 and surface 744 of electrode 740 so as to form a brazed joint between insulator 760 and electrode 740. Braze material element 782 has a predetermined size which produces a brazed joint of sufficient strength without exceeding the maximum shear strength of the brazed joint components. As with FIG. 30, although the braze alloy 782 is depicted as a single round deposition, other quantities, sizes and shapes are contemplated. Preferred distribution and sizing is as discussed above.

FIGS. 44 through 47 depict the distal portion 800 of an ablator electrode designed for use with a resectoscope. Electrode assembly 780 is affixed to elbows 784 which are affixed to the distal ends of wires 786 by laser welding. Wires 786, elbows 784, exposed regions of protrusions 746 of electrode 740, and tubular portions 772 of insulator 760 are covered by a dielectric coating. In a preferred embodiment the dielectric coating is a heat shrink tubing formed from polyolefin, PTFE, PET, or another suitable polymeric material.

Industrial Applicability

The present invention replaces mechanical fastening means, epoxies and other high-temperature adhesives for connecting electrode(s) to insulator(s) with brazed joints to yield electrosurgical devices capable of safely and reliably operating at high power densities and elevated temperatures without thermal failure of the bonds between the electrode and the insulator. The use of brazed joints further permits the construction of miniaturized, compact electrosurgical devices, of both monopolar or bipolar configurations, having utility in a number of divergent fields, from arthroscopy to otolaryngology to oncology, and applicable to both laparoscopic and open surgery techniques. Thus, active electrodes and electrosurgical devices of the present invention maximize efficiency, safety and reliability while minimizing manufacturing cost and device profile.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed:

1. An active electrode assembly constructed for connection to an electrosurgical device, said active electrode assembly comprising:
   a) an electrode fabricated entirely of a metal material, wherein said electrode has a distal portion comprising an electrically active surface and a proximal portion constructed to connect with the distal end of an electrosurgical device and have an electrical connection to an external power supply such that current flows from said external power supply to said electrically active surface; and
   b) an insulator fabricated entirely of a non-conductive material, said insulator having proximal and distal ends, wherein said insulator is disposed about the distal portion of said metal electrode and is snugly fit against said electrode, such that the distal portion of said electrically active surface extends distally beyond the distal end of said insulator;
   wherein said electrode and insulator are permanently affixed directly to each other by means of a brazed joint arising from a braze material disposed between said electrode and said insulator
   further wherein the coefficient of thermal expansion of the metal electrode material is more than half (0.5×) and less than twice (2×) the coefficient of thermal expansion of the non-conductive insulator material.

2. The electrode assembly of claim 1, wherein:
   (i) said metal electrode includes a radially projecting metal flange disposed between said proximal and distal portions, said radially projecting metal flange having opposed proximal and distal surfaces;
   (ii) the proximal end of said non-conductive insulator is a radially projecting lip having opposed proximal and distal surfaces; and
   (iii) the fit between said electrode and insulator is characterized by the engagement of the proximal surface of said radially projecting non-conductive insulator lip and the distal surface of said radially projecting metal electrode flange; further
   wherein said braze material is disposed between said radially projecting metal electrode flange and said radially projecting non-conductive insulator lip.

3. The active electrode assembly of claim 1, wherein the metal electrode is relatively cylindrical and the insulator has a mating tubular profile.

4. The active electrode assembly of claim 1, wherein the proximal end of said insulator is planar.

5. The active electrode assembly of claim 1, wherein said insulator has an outer diameter of 4 millimeters or less.

6. The active electrode assembly of claim 1, wherein said insulator has a wall thickness that ranges between 0.3 and 0.8 millimeters.

7. The active electrode assembly of claim 1, wherein said braze material is a metal alloy of copper, gold, silver, nickel, chromium, cobalt, molybdenum, platinum, palladium, titanium, silicon, or vanadium.

8. The active electrode assembly of claim 1, wherein said braze material is deposited as a braze spot having a maximum width or diameter of 3 mm or less.

9. The active electrode assembly of claim 1, wherein said braze material is deposited as a braze spot having a maximum width or diameter of 1.5 mm or less.

10. The active electrode assembly of claim 1, wherein said braze material is deposited as a braze spot having an area of 7 mm2 or less.

11. The active electrode assembly of claim 1, wherein said braze material is deposited as a braze spot having an area of 1.8 mm2 or less.

12. The active electrode assembly of claim 1, wherein said metal material is selected from the group consisting of stainless steel, aluminum, nickel, titanium, molybdenum and tungsten.

13. The active electrode assembly of claim 1, wherein said metal material is a 400 series stainless steel.

14. The active electrode assembly of claim 1, wherein said non-conductive material is a biocompatible ceramic.

15. The active electrode assembly of claim 14, wherein said ceramic material comprises an oxide selected from the group consisting of alumina, beryllia, ceria, and zirconia.

16. The electrode of claim 1, further comprising a dielectric coating disposed about the proximal portion of said metal electrode and the proximal end of said non-conductive insulator.

17. The electrode of claim 16, wherein said dielectric coating comprises a heat shrink tubing having a high service temperature.

18. The active electrode assembly of claim 1, further comprising:
   c) a second electrode comprising a metal ring having proximal and distal ends, wherein said second electrode is also disposed about said nonconductive insulator.

19. The active electrode assembly of claim 18, wherein said second electrode is not connected to any power supply and thus acts as a floating electrode.

20. The active electrode assembly of claim 18, wherein said second electrode is connected to a power supply and thus acts as a return electrode.

21. The active electrode assembly of claim 18, wherein said second electrode is fabricated from stainless steel, aluminum, nickel, titanium, molybdenum or tungsten.

22. An electrosurgical device comprising:
   a) the active electrode assembly of claim 1;
   b) an elongate tubular element affixed at its distal end to the proximal portion of said metal electrode and at its proximal end to an external power supply, wherein said elongate tubular element houses a cabling capable of connecting said active electrode to said power supply, and
   c) an optional dielectric coating disposed about the exterior of the tubular element, the proximal portion of the electrode, and a proximal end of said insulator.

23. The electrosurgical device of claim 22, configured for bulk vaporization of tissue.

24. The electrosurgical device of claim 22, configured for the thermal treatment of tissue.

25. The electrosurgical device of claim 22, configured for the resection of tissue.

26. A layered electrode assembly constructed for connection to an electrosurgical device introduced by means of a resectoscope, said assembly comprising:
   a) an electrode fabricated entirely of a metal material, wherein said electrode has a planar first surface constructed to connect with the distal end of an electrosurgical device and have an electrical connection to an external power supply, and an opposing non-planar electrically active second surface such that current flows from said external power supply to said opposing non-planar electrically active second surface;
   b) an insulator fabricated entirely of a non-conductive material, said insulator having a planar first surface and an opposing second surface, wherein said planar first surface of said insulator approximates the size and shape of said planar first surface of said metal electrode;
wherein said electrode and insulator are configured to fit together and are permanently affixed directly to each other by means of a brazed joint arising from a braze alloy disposed between said planar first surface of said electrode and said planar first surface of said insulator, further wherein the coefficient of thermal expansion of the metal electrode material is more than half (0.5×) and less than twice (2×) the coefficient of thermal expansion of the non-conductive insulator material.

27. The layered electrode assembly of claim 26, further comprising a second electrode having a planar first surface and an opposing second surface, wherein the planar first surface of said second electrode approximates the size and shape of the planar first surface of said insulator, further wherein said second electrode and said insulator are configured to fit together and are permanently affixed directly to each other by means of a brazed joint arising from a braze alloy disposed between the planar first surface of said second electrode and the opposing second surface of said insulator.

28. The layered electrode assembly of claim 26, wherein said metal electrode and insulator are provided with one or more mating openings through which one or more electrical power conductors may pass.

29. The layered electrode assembly of claim 26, wherein the opposing nonplanar electrically active second surface of said metal electrode comprises an array of protuberances.

30. The layered electrode assembly of claim 29, wherein said protuberances are ribs.

31. The layered electrode assembly of claim 26, wherein the opposing non-planar electrically active second surface of said metal electrode comprises a curved surface.

32. The layered electrode assembly of claim 26, wherein said metal electrode comprises a hemisphere.

33. The layered electrode assembly of claim 26, wherein said metal material is selected from the group consisting of stainless steel, aluminum, nickel, titanium, molybdenum and tungsten and said non-conductive material is a biocompatible ceramic.

34. The layered electrode assembly of claim 26, wherein said metal material is a 400 series stainless steel and said non-conductive material is a biocompatible ceramic comprising an oxide selected from the group consisting of alumina, beryllia, ceria, and zirconia.

35. An electrosurgical device comprising:
a) at least one active electrode fabricated entirely of a metal material and having anelectrically active surface at its distal end, wherein said at least one active metalelectrode is constructed to connect with a suitable radio frequency generator such that currentflows from said radio frequency generator to said electrically active surface of said metal material; and
b) an insulator fabricated entirely of a non-conductive ceramic material; wherein said ceramic insulator is directly affixed to said at least one metal electrode by brazing,
further wherein the coefficient of thermal expansion of the metal electrode material is more than half (0.5×) and less than twice (2×) the coefficient of thermal expansion of the non-conductive ceramic material.

* * * * *